(12) United States Patent
Boutoussov et al.

(10) Patent No.: US 8,152,797 B2
(45) Date of Patent: *Apr. 10, 2012

(54) ELECTROMAGNETIC ENERGY OUTPUT SYSTEM

(75) Inventors: Dmitri Boutoussov, Dana Point, CA (US); Jeffrey W. Jones, Robertson, WY (US); Julio Guillermo Cely, Irvine, CA (US); Ioana M. Rizoiu, San Clamente, CA (US); Manvel Artyom Andriasyan, Irvine, CA (US)

(73) Assignee: Biolase Technology, Inc., Irvine, CA (US)

( * ) Notice: Subject to any disclaimer, the term of this patent is extended or adjusted under 35 U.S.C. 154(b) by 232 days.

This patent is subject to a terminal disclaimer.

(21) Appl. No.: 12/632,774

(22) Filed: Dec. 7, 2009

(65) Prior Publication Data
US 2010/0145323 A1    Jun. 10, 2010

Related U.S. Application Data

(63) Continuation of application No. 11/800,434, filed on May 3, 2007, which is a continuation of application No. 11/698,345, filed on Jan. 25, 2007.

(60) Provisional application No. 60/898,022, filed on Jan. 26, 2007.

(51) Int. Cl.
*A61B 18/20* (2006.01)
(52) U.S. Cl. ............................................ 606/13; 606/16
(58) Field of Classification Search .............. 606/3–27; 607/88–95; 600/101
See application file for complete search history.

(56) References Cited

U.S. PATENT DOCUMENTS

| | | |
|---|---|---|
| 4,562,832 A | 1/1986 | Wilder et al. |
| 4,770,811 A | 9/1988 | Myers |
| 4,852,567 A | 8/1989 | Sinofsky |
| 5,009,655 A | 4/1991 | Daignault, Jr. et al. |
| 5,086,378 A | 2/1992 | Prince |
| 5,237,331 A | 8/1993 | Henderson et al. |
| 5,374,266 A | 12/1994 | Kataoka et al. |
| 5,498,935 A | 3/1996 | McMahan et al. |
| 5,554,172 A | 9/1996 | Horner et al. |
| 5,570,182 A | 10/1996 | Nathel et al. |
| 5,741,247 A | 4/1998 | Rizoiu et al. |
| 6,022,316 A | 2/2000 | Eppstein et al. |
| 6,183,434 B1 | 2/2001 | Eppstein |
| 6,223,987 B1 | 5/2001 | Knowles et al. |
| 6,231,567 B1 | 5/2001 | Rizoiu et al. |
| 6,254,530 B1 | 7/2001 | Ryan, Jr. |
| 6,315,772 B1 | 11/2001 | Marchitto et al. |

(Continued)

FOREIGN PATENT DOCUMENTS

DE    3840126 A1    5/1990
(Continued)

OTHER PUBLICATIONS

International Search Report and Written Opinion, Application No. PCT/US06/21691, mailed Dec. 1, 2006.

(Continued)

*Primary Examiner* — Ahmed Farah
(74) *Attorney, Agent, or Firm* — Stout, Uxa, Buyan & Mullins, LLP

(57) ABSTRACT

An apparatus having an excitation source that includes at least one laser diode and also having a handpiece with a disposable, bendable tip cannula is disclosed.

20 Claims, 19 Drawing Sheets

U.S. PATENT DOCUMENTS

| | | | |
|---|---|---|---|
| 6,527,716 B1 | 3/2003 | Eppstein | |
| 6,648,854 B1 | 11/2003 | Patterson et al. | |
| 6,648,902 B2 | 11/2003 | Colgan et al. | |
| 6,730,076 B2 | 5/2004 | Hickingbotham | |
| 6,802,838 B2 | 10/2004 | Loeb et al. | |
| 6,853,863 B2 | 2/2005 | Carter et al. | |
| 6,878,899 B2 | 4/2005 | Smart | |
| 6,902,290 B2 | 6/2005 | Watts et al. | |
| 7,125,416 B2 | 10/2006 | Kent et al. | |
| 7,238,178 B2 | 7/2007 | Maschke | |
| 7,309,344 B2 | 12/2007 | Bakos et al. | |
| 7,695,469 B2 * | 4/2010 | Boutoussov et al. | 606/13 |
| 2002/0149324 A1 | 10/2002 | Rizoiu et al. | |
| 2003/0227953 A1 | 12/2003 | Hsia et al. | |
| 2005/0283143 A1 | 12/2005 | Rizoiu | |
| 2006/0281042 A1 | 12/2006 | Rizoiu et al. | |

FOREIGN PATENT DOCUMENTS

| | | |
|---|---|---|
| GB | 2297610 A | 8/1996 |
| JP | 5200045 A | 8/1993 |
| JP | 5506601 A | 9/1993 |
| JP | 11511386 A | 10/1999 |
| WO | 9004358 A1 | 5/1990 |

OTHER PUBLICATIONS

International Search Report and Written Opinion, Application No. PCT/US08/51967, mailed May 23, 2008.

International Search Report and Written Opinion, Application No. PCT/US08/51963, mailed Jun. 30, 2008.

International Search Report and Written Opinion, Application No. PCT/US08/51918, mailed Nov. 6, 2008.

International Preliminary Report on Patentability, Application No. PCT/US08/51963, mailed Aug. 10, 2009.

Supplementary European Search Report, EP 05711358 (PCT/US2005/000852), mailed Feb. 8, 2010.

Rizoiu, Ioana and Levy, Guy C. "Efficiency of Bone Ablation with an Nd:YAG Laser Beam Delievered with a Cooling Spray" SPIE vol. 1882 Laser-Tissue Interaction IV (1993), pp. 316-321.

* cited by examiner

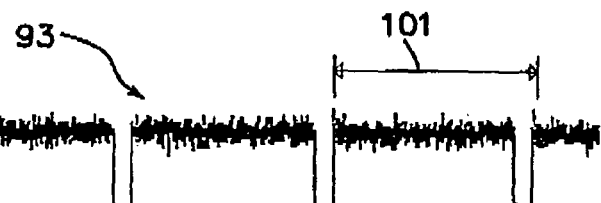
FIG. 4A
FIG. 4B
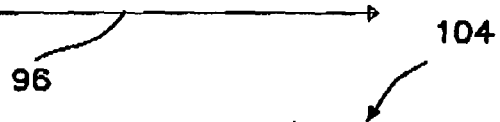
FIG. 5

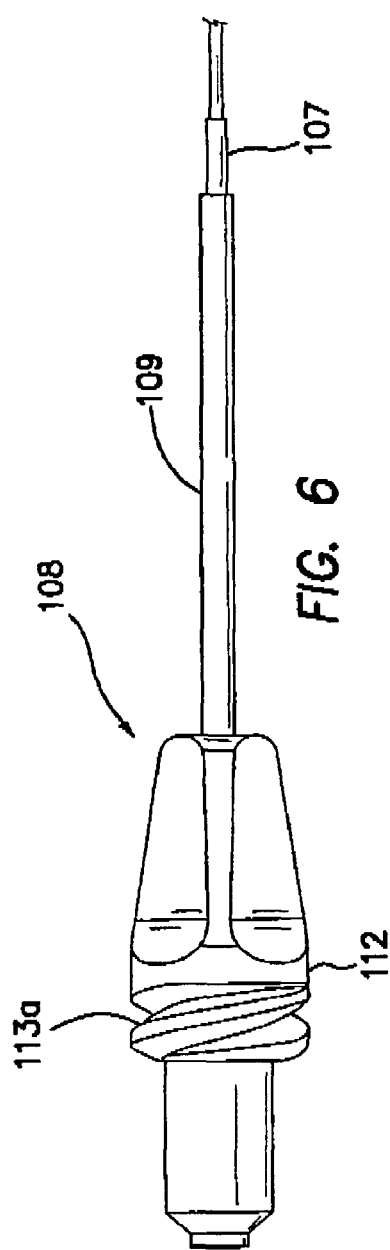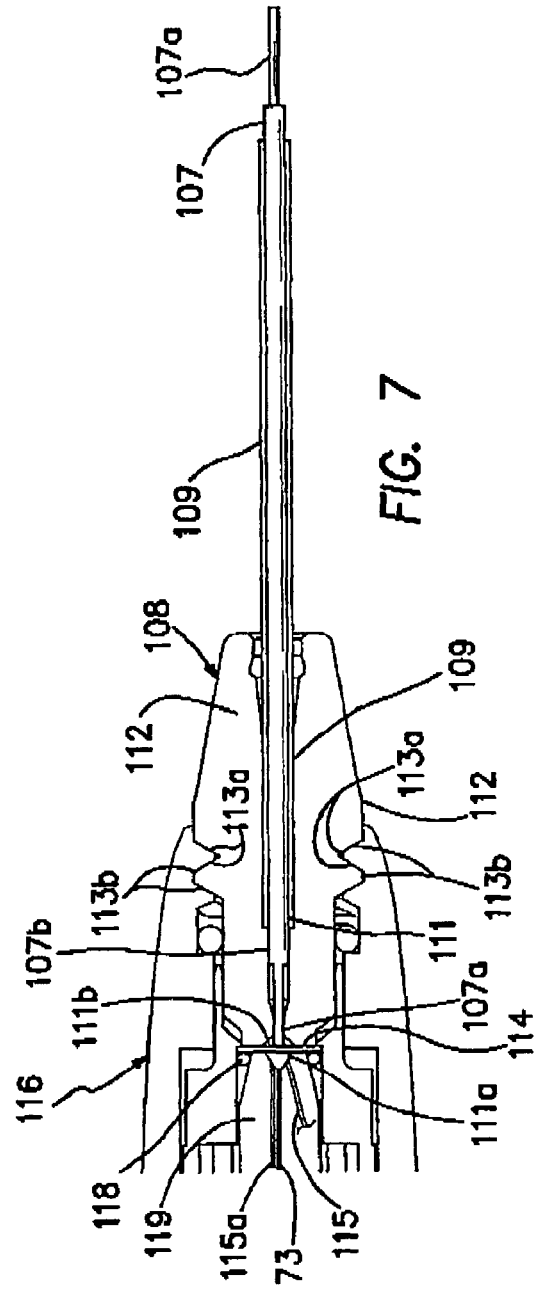

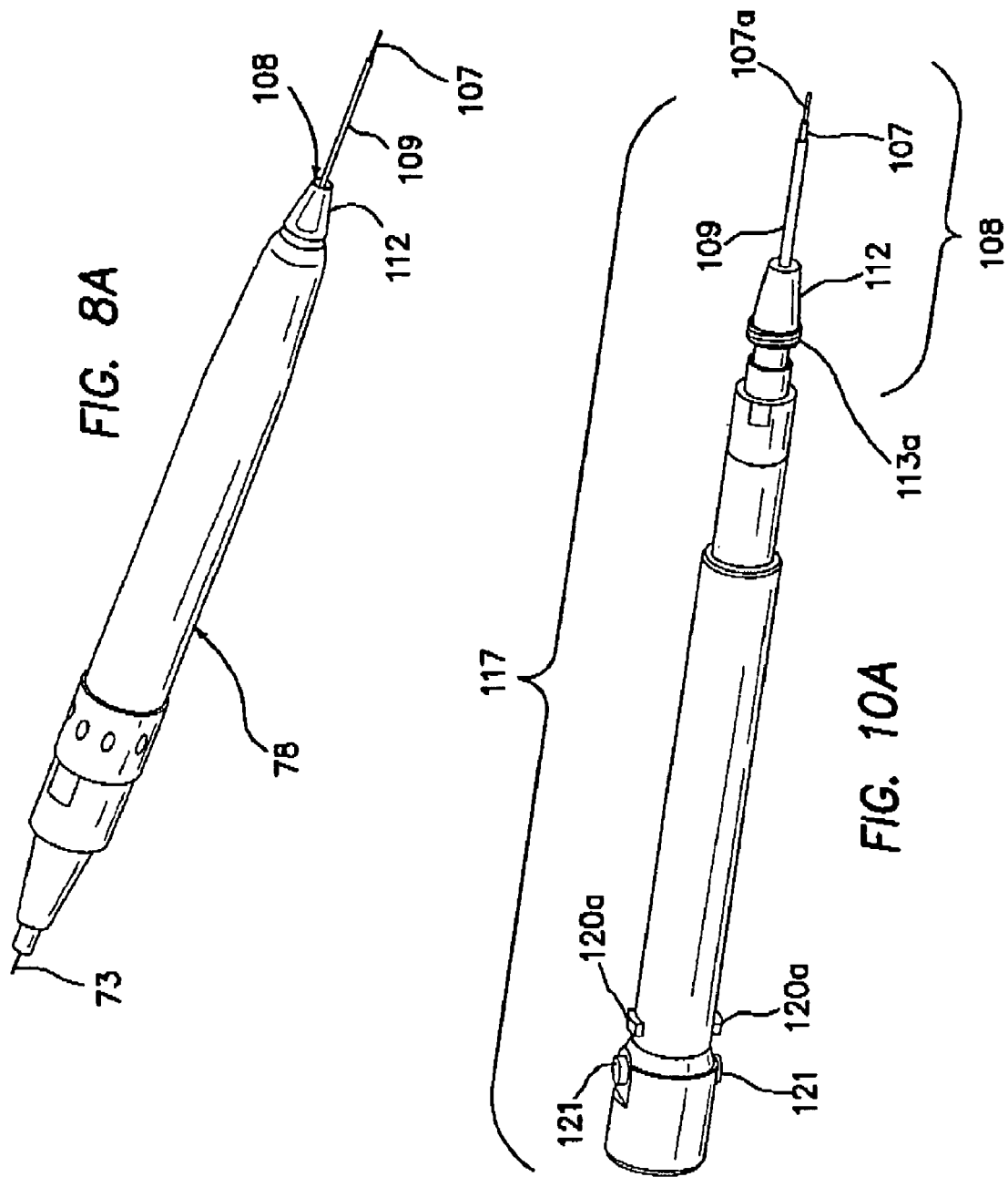

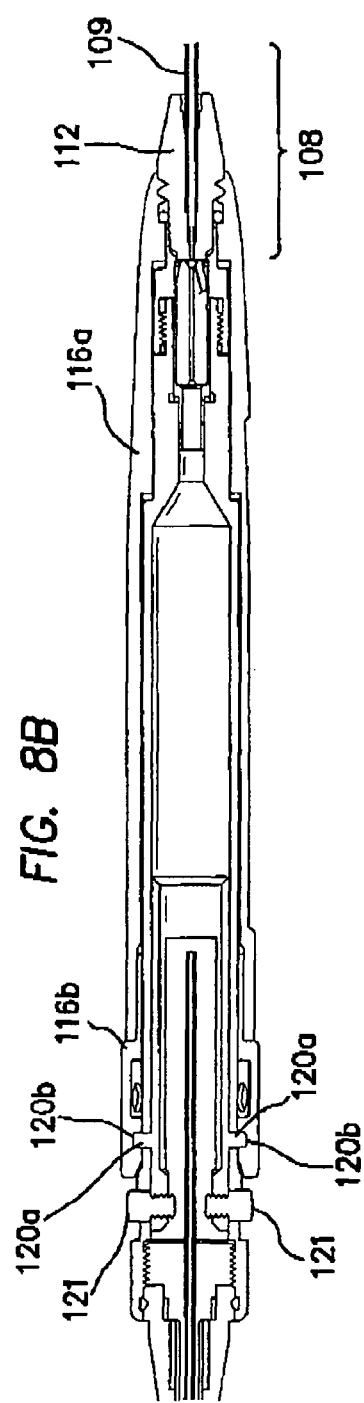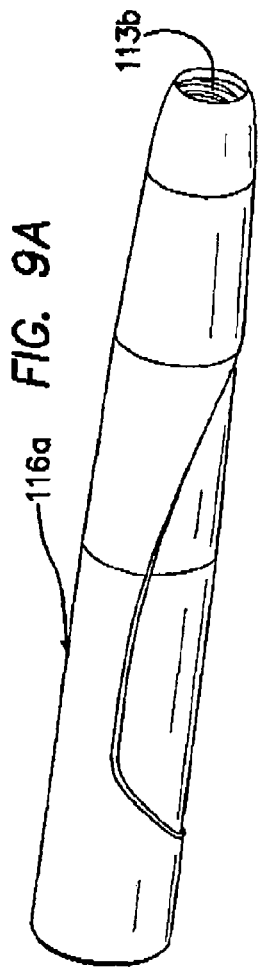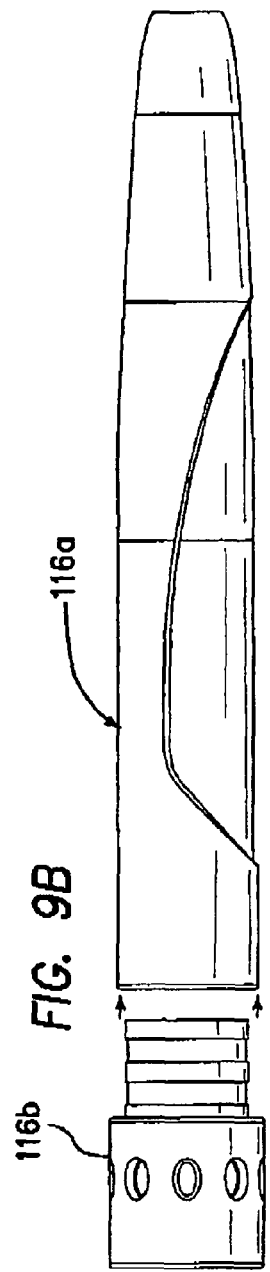

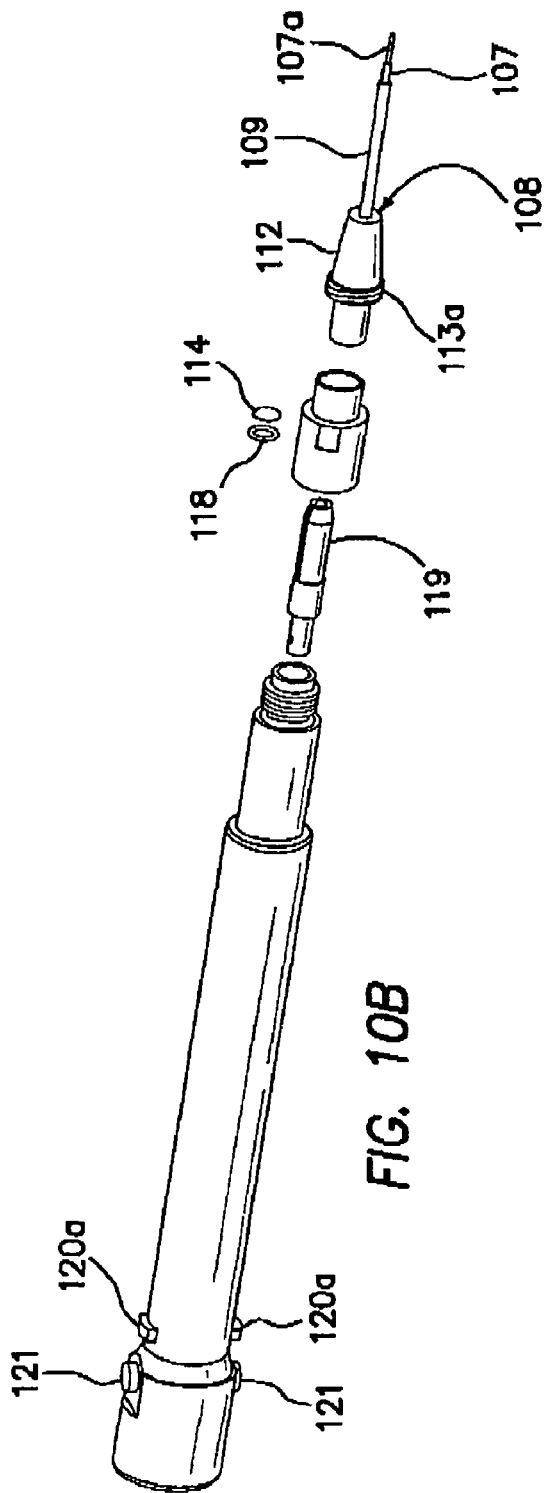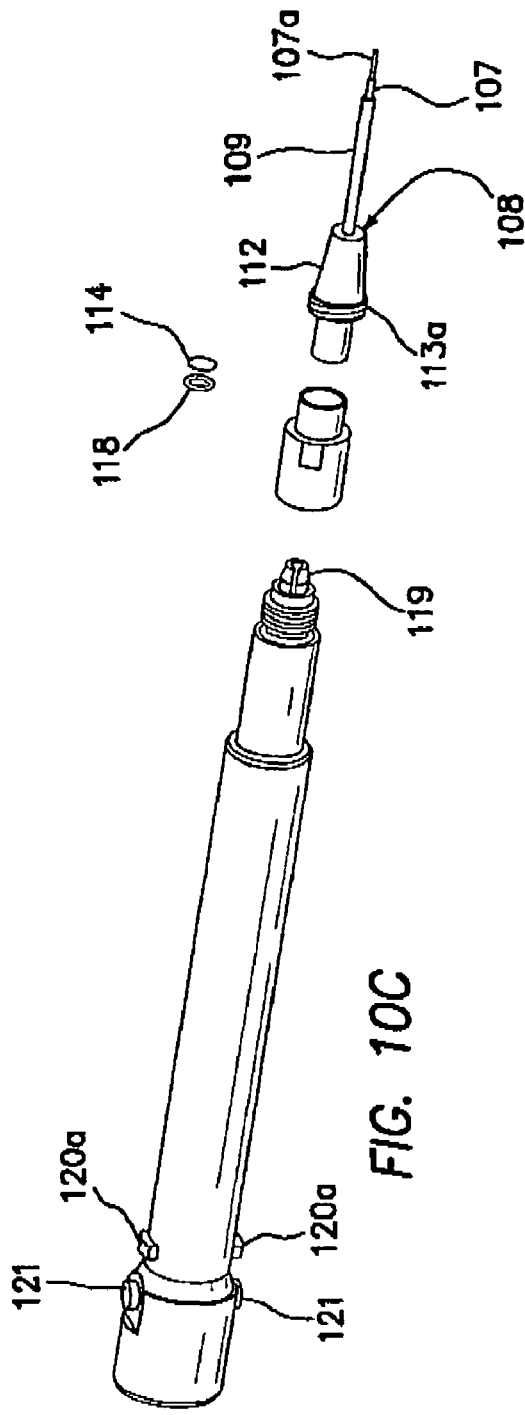

| | TIP VIEW | NAME | CODE | CANNULA (TUBE) OD, mm | CANNULA (TUBE) LENGTH, mm | FIBER LENGTH, mm | TIP PRICE $ | SURGICAL KIT | PERIO KIT | ENDO KIT | P/N FOR KIT |
|---|---|---|---|---|---|---|---|---|---|---|---|
| 1 | | ezTip Surgical, 400um | E4-4 | 1.3 | 15 | 4 | 8 | 25 | | | 74000XX |
| 2 | | ezTip Perio, 7mm / 400um | E4-6 | 1.3 | 15 | 7 | 9 | | 15 | | 74000XX |
| 3 | | ezTip Perio, 9mm / 400um | E4-9 | 1.3 | 15 | 9 | 10 | | 10 | | |
| 4 | | ezTip Surgical, 300um | E3-4 | 1.1 | 15 | 4 | 8 | 25 | | | 7400XX |
| 5 | | ezTip Perio, 7mm / 300um | E3-7 | 1.1 | 15 | 7 | 9 | | 15 | | 7400XX |
| 6 | | ezTip Perio, 9mm / 300um | E3-9 | 1.1 | 15 | 9 | 10 | | 10 | | |
| 7 | | ezTip Surgical, 200um | E2-4 | 0.9 | 15 | 4 | 8 | 25 | | | 7400XX |
| 8 | | ezTip Endo, 14mm / 200um | E2-14 | 0.9 | 15 | 14 | 12 | | | 25 | 7400XX |

TIPS TYPES

FIG. 14

ELECTROMAGNETIC ENERGY OUTPUT SYSTEM

CROSS-REFERENCE TO RELATED APPLICATIONS

This application is a continuation of U.S. application Ser. No. 11/800,434, filed May 3, 2007 and entitled ELECTROMAGNETIC ENERGY OUTPUT SYSTEM, which claims priority to U.S. Provisional Application No. 60/898,022, filed on Jan. 26, 2007 and which is a continuation-in-part of U.S. application Ser. No. 11/698,345, filed Jan. 25, 2007 and entitled ELECTROMAGNETIC ENERGY OUTPUT SYSTEM, the entire contents all of which are hereby incorporated by reference.

BACKGROUND OF THE INVENTION

1. Field of the Invention

The present invention relates generally to devices for generating output optical energy distributions and, more particularly, to lasers.

2. Description of Related Art

A variety of laser systems have existed in the prior art. A solid-state laser system generally comprises a laser rod for emitting coherent light and a stimulation source for stimulating the laser rod to emit the coherent light. Flashlamps are typically used as stimulation sources for laser systems, for example, but diodes may be used as well for the excitation source. The use of diodes for generating light amplification by stimulated emission is discussed in the book Solid-State Laser Engineering, Fourth Extensively Revised and Updated Edition, by Walter Koechner, published in 1996, the contents of which are expressly incorporated herein by reference.

With reference to FIG. 1, a conventional laser assembly 25 may comprise a housing 27 containing a laser module 29, which is connected by way of an optical connector 31 to a trunk fiber 33. The optical connector 31 is typically disposed within and concealed by a portion of the housing 27 and, further, is typically constructed to facilitate attachment and removal of the trunk fiber 33 to and from the housing 27. Moreover, in the illustrated prior-art example, the trunk fiber 33 extends in an uninterrupted fashion from the housing 27 up to and through a handpiece 35. Furthermore, the trunk fiber 33 continues in an uninterrupted fashion from the handpiece 35 through a pre-bent tip cannula 38 and terminates at an energy output end 40 of the trunk fiber 33. The pre-bent tip cannula 38 comprises a rigid plastic or a stainless steel material.

A spool (not shown) can be disposed in close proximity to the optical connector 31, for storing extra trunk fiber 33. The spool can be secured to the housing 27 to provide a user with access and to enable the user to increase a length of the trunk fiber 33 by advancing addition trunk fiber 33 from the spool toward the handpiece 35. In typical implementations, the energy output end 40 of the trunk fiber 33 can exhibit signs of wear or damage after use, and thus should be replaced on a regular and frequent basis. To this end, after each use, the user will typically need to cleave a portion (e.g., between 3 and 10 millimeters) off of the energy output end 40 of the trunk fiber 33 and advance an additional length of trunk fiber 33 from the spool to compensate for the decrease in length of the trunk fiber 33 caused by the cleaving. Of course, to facilitate this functionality, the trunk fiber 33 must be slidably disposed, and cannot be permanently affixed such as by an adhesive, within the pre-pent tip cannula 38. Using this technique, a trunk fiber 33 length of, for example, 10 to 12 feet can be maintained. Additionally, for sanitation purposes, the pre-bent tip cannula and any other appropriate components are typically sterilized, such as by autoclaving, on a regular and frequent basis.

FIG. 2 illustrates a plot of energy versus time for an output optical energy waveform 43 of a prior-art laser, such as the conventional laser assembly 25 depicted in FIG. 1. The output optical energy waveform 43 may be generated by a compact diode laser, such as a SIROlaser, manufactured by Sirona Dental Systems GmbH, of Germany, having a URL of www-.sirona.com, operable at a wavelength of 980 nanometers and a repetition rate of about 10 kHz, and having an average power output, defined as the power delivered over a predetermined period of time, varying from 0.5 to 7 W. Each pulse of the depicted output optical energy waveform 43 has a pulse duration 46 and a pulse interval 48. In the illustrated example, the output optical energy waveform 43 can be generated such that the pulse duration 46 can have a value of about 50 microseconds and the pulse interval 48 can also have a value of about 50 microseconds. According to the exemplary depiction, the output optical energy waveform 43 can be said to have a pulse period 51 of about 100 microseconds, and, furthermore, the output optical energy waveform 43 can be said to have a pulse duty cycle, defined as the pulse duration 46 divided by the pulse interval 48, of about 50%. The pulse duration 46 and the pulse duration 48 of this exemplary prior-art system cannot be independently adjusted.

Another prior-art system is the LaserSmile™ laser, manufactured by Biolase Technology, Inc., of Irvine, Calif., having a URL of www.biolase.com. This laser can be operated at a wavelength of 810 nanometers and a repetition rate of, for example, about 0.01 to about 5 Hz, with corresponding pulse durations of about 0.02 to about 9.9 seconds, and with an average power output up to about 10 W. Output optical energy waveforms from the laser can have pulse duty cycles of, for example, between 10% and 50%. Additionally, while being independently adjustable, the pulse duration and pulse interval of the laser's output optical energy waveform tend to be relatively large and not adequately or optimally suited for a number of soft tissue cutting procedures, such as procedures designed to minimize an impartation of thermal energy into the target soft tissue.

SUMMARY OF THE INVENTION

The present invention provides an apparatus having an excitation source that includes at least one laser diode and also having a handpiece with a disposable, bendable tip cannula.

While the apparatus and method have or will be described for the sake of grammatical fluidity with functional explanations, it is to be expressly understood that the claims, unless expressly formulated under 35 USC 112, are not to be construed as necessarily limited in any way by the construction of "means" or "steps" limitations, but are to be accorded the full scope of the meaning and equivalents of the definition provided by the claims under the judicial doctrine of equivalents, and in the case where the claims are expressly formulated under 35 USC 112 are to be accorded full statutory equivalents under 35 USC 112.

Any feature or combination of features described herein are included within the scope of the present invention provided that the features included in any such combination are not mutually inconsistent as will be apparent from the context, this specification, and the knowledge of one skilled in the art. In addition, any feature or combination of features may be specifically excluded from any embodiment of the present invention. For purposes of summarizing the present invention, certain aspects, advantages and novel features of the present invention are described. Of course, it is to be understood that not necessarily all such aspects, advantages or features will be embodied in any particular implementation of the present invention. Additional advantages and aspects of the present invention are apparent in the following detailed description and claims that follow.

BRIEF DESCRIPTION OF THE FIGURES

FIGS. 4A and 5 illustrate plots of energy versus time for output optical energy waveforms, according to the present invention, that can be outputted by an electromagnetic energy output system such as the laser module depicted in FIG. 3;

FIG. 4B is a magnified view of the plot of energy versus time for the output optical energy waveform of FIG. 4A;

FIG. 6 is a side-elevation view of an exemplary output tip comprising an output fiberoptic, a bendable tip cannula, and a ferrule;

FIG. 7 is a cross-sectional view of the output tip shown in FIG. 6, secured to a handpiece;

FIG. 8A is a side-elevation view of the output tip of FIG. 6 connected to a handpiece;

FIG. 8B is a cross-sectional view of the assembly of FIG. 8A;

FIG. 9A shows a side-elevation view of an outer layer of the handpiece of FIGS. 8A and 8B;

FIG. 9B shows a side-elevation view of the outer layer along with a coupling member;

FIG. 10A is a perspective view depicting an inner assembly, which is also shown in FIG. 8B and which includes the output tip;

FIG. 10B is an exploded, perspective view of the assembly of FIG. 10A;

FIG. 10C is a partially-assembled view of the components depicted in FIG. 10B;

FIG. 14 shows examples of a number of typical bendable tip cannulas according to the present invention;

DETAILED DESCRIPTION OF THE PRESENT INVENTION

Figure 1:
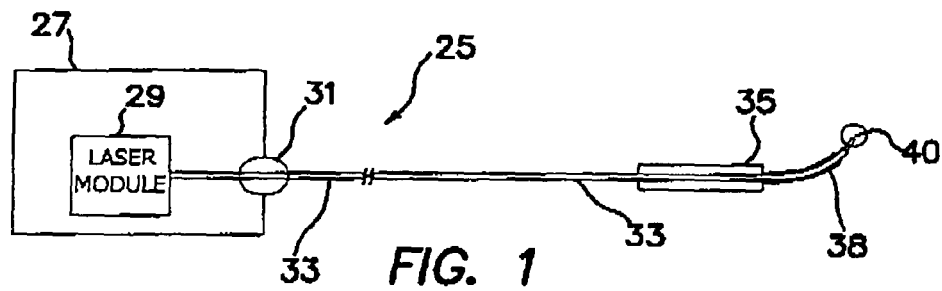
FIG. 1 shows a conventional laser assembly.
Figure 2:
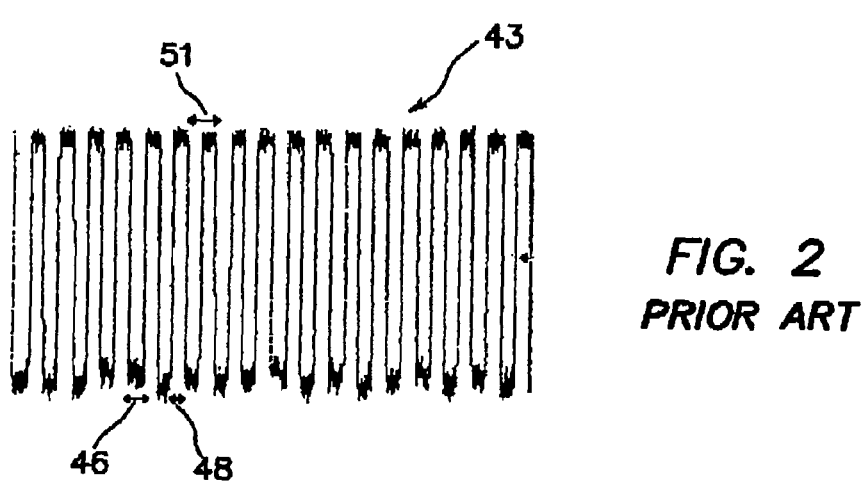
FIG. 2 illustrates a plot of energy versus time for an output optical energy waveform of a prior-art laser.

Reference will now be made in detail to particular embodiments of the invention, examples of which are illustrated in the accompanying drawings. Wherever possible, the same or similar reference numbers are used in the drawings and the description to refer to the same or like parts. It should be noted that the drawings are in simplified form and are not to precise scale. In reference to the disclosure herein, for purposes of convenience and clarity only, directional terms, such as, top, bottom, left, right, up, down, over, above, below, beneath, rear, and front, are used with respect to the accompanying drawings. Such directional terms should not be construed to limit the scope of the invention in any manner.

Although the disclosure herein refers to certain illustrated embodiments, it is to be understood that these embodiments are presented by way of example and not by way of limitation. The intent of this disclosure, while discussing exemplary embodiments, is that the following detailed description be construed to cover all modifications, alternatives, and equivalents of the embodiments as may fall within the spirit and scope of the invention as defined by the appended claims.

An electromagnetic energy output device is disclosed for implementing procedures on hard or soft tissue. The electromagnetic energy output device can be configured, for example, to be particularly suited for soft tissue cutting or ablating procedures, and also for decontamination, cleaning periodontal pockets, pain reduction, and biostimulation procedures.

Figure 3:
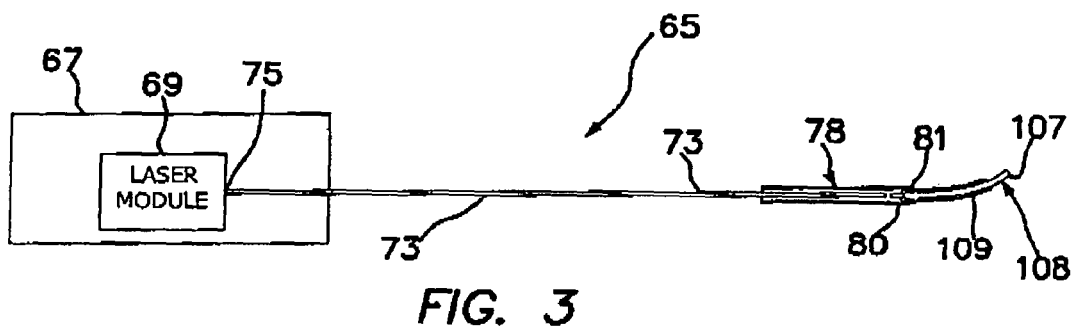
FIG. 3 depicts an electromagnetic energy output device according to the present invention.

With reference to FIG. 3, an embodiment of the current invention comprises an electromagnetic energy output device 65 having a system 67, such as a diode laser system. The system 67 in the illustrated embodiment can comprise a laser module 69, which, in accordance with one aspect of the present invention, can be directly coupled to a trunk optical fiber 73. According to one implementation and one aspect of the invention, the trunk optical fiber 73 can be permanently coupled to the system 67. According to another embodiment and aspect of the invention, the trunk optical fiber 73 can also, or alternatively, be permanently coupled to the laser module 69 within the system 67.

The trunk optical fiber 73 in the illustrated embodiment, and according to another aspect of the invention, extends from a permanent connection 75 at the laser module 69 all of the way to a handpiece 78. Furthermore, in a typical embodiment, the trunk optical fiber 73 extends a further distance through at least a part of the handpiece 78. In the illustrated embodiment, the trunk optical fiber 73 extends through substantially all of the handpiece 78 and terminates at an energy output end 80 of the trunk fiber 73, in a vicinity of a distal handpiece end 81 of the handpiece 78.

A diode (not shown) within the laser module 69 can be driven by a diode current, which can comprise a predetermined pulse shape and a predetermined frequency. The diode current can drive a diode, or diode array, at the predetermined frequency, to thereby produce an output diode light distribution having, for example, substantially the same frequency as the diode current. This output diode light distribution from the diode can drive a laser rod (not shown) to produce coherent light at substantially the same predetermined frequency as the diode current. The coherent light generated by the laser rod can have, for example, an output optical energy distribution over time that generally corresponds to the pulse shape of the diode current. The pulse shape of the output optical energy distribution over time typically comprise a relatively steep rising energy that ramps to a maximum energy level followed by a subsequent decreasing energy over time.

The laser module 69 may comprise a solid-state laser rod pumping module and a stack-type semiconductor laser. The semiconductor laser can be based on a semiconductor gain media, where optical gain is generally achieved by stimulated emission at an interband transition under conditions of an inversion (i.e., high carrier density in the conduction band). The semiconductor laser can be a laser diode, which is pumped by an electrical current in a region where n-doped and p-doped semiconductor materials meet. In certain embodiments, optically pumped semiconductor lasers, where carriers are generated by absorbed pump light, can be used. In the case of, for example, a stack-type semiconductor laser, it can include a plurality of bar-shaped components that are stacked in a direction parallel to the axis of a solid-state laser rod. Each bar-shaped component can include a plurality of laser-light-emitting portions that are aligned and integrated in a direction orthogonal to the axis of the solid-state laser rod. The large divergence angle of the stack-type semiconductor can be compensated by including a light focusing component for focusing laser light emitted out of the stack-type semiconductor laser, and the focused light can be guided by a laser light guiding component disposed in a diffusive reflection tube. Thus, a light guiding component can guide focused light onto the solid-state laser rod located within the diffusive reflective tube, while maintaining the length of one side of the cross section of the guided light.

The semiconductor laser or other optoelectronic device can comprise, for example, an Indium Gallium Arsenide (GaAs) material. In an exemplary implementation, the gain medium can comprise a laser rod, such as a configuration comprising an active heterostructure and substrate of AlGa(In)As/GaAs, wherein the Ga of the active heterostructure can be substituted for and/or combined with In. Another exemplary implementation can comprise AlGaInP(As)/GaAs, wherein the P of the active heterostructure can be substituted for and/or combined.

FIG. 4A illustrates a plot of energy versus time for an output optical energy waveform 93, according to the present invention, that can be outputted by an electromagnetic energy output system, such as the laser module 69 depicted in FIG. 3. FIG. 4B is a magnified view of the plot of energy versus time for the output optical energy waveform 93 of FIG. 4A.

Each of the pulses of the output optical energy waveform 93 comprises a plurality of micropulses. The micropulses correspond to population inversions within the laser rod as coherent light is generated by stimulated emission. Particles, such as electrons, associated with impurities of the laser rod absorb energy from the impinging incoherent radiation and rise to higher valence states. The particles that rise to metastable levels remain at this level for periods of time until, for example, energy particles of the radiation excite stimulated transitions. The stimulation of a particle in the metastable level by an energy particle results in both of the particles decaying to a ground state and an emission of twin coherent photons (particles of energy). The twin coherent photons can resonate through the laser rod between mirrors at opposing ends of the laser rod, and can stimulate other particles on the metastable level, to thereby generate subsequent twin coherent photon emissions. This process is referred to as light amplification by stimulated emission. With this process, a twin pair of coherent photons will contact two particles on the metastable level, to thereby yield four coherent photons. Subsequently, the four coherent photons will collide with other particles on the metastable level to thereby yield eight coherent photons.

The amplification effect will continue until a majority of particles, which were raised to the metastable level by the stimulating incoherent light from the diode, have decayed back to the ground state. The decay of a majority of particles from the metastable state to the ground state results in the generation of a large number of photons, corresponding to an upwardly rising micropulse. As the particles on the ground level are again stimulated back up to the metastable state, the number of photons being emitted decreases, corresponding to a downward slope in the micropulse. The micropulse continues to decline, corresponding to a decrease in the emission of coherent photons by the laser system. The number of particles stimulated to the metastable level increases to an amount where the stimulated emissions occur at a level sufficient to increase the number of coherent photons generated. As the generation of coherent photons increases, and particles on the metastable level decay, the number of coherent photons increases, corresponding to an upwardly rising micropulse.

The output optical energy waveform 93 according to an aspect of the invention is generated by a diode laser to have a wavelength, pulse, and power density suitable for cutting and ablating, for example, soft tissue. The diode light pump or the at least one diode can comprise a diode array, and the diode or diode array can be optically aligned to side pump the gain medium. In one implementation, the diode light pump can be placed, for example, within an optical cavity so that the diode or diode array is optically aligned to side pump the gain medium. Generation of the output optical energy waveform 93 can be accomplished, for example, in the TEMoo mode to attenuate or overcome thermal effects.

With reference to FIGS. 4A and 4B, the output optical energy waveform 93 according to an aspect of the invention is generated by a diode laser to have a wavelength of 940 microseconds, and can be delivered, for example, in a CW (continuous wave) or a QCW (quasi-continuous wave) mode of operation. As presently embodied, the output optical energy waveform 93 is delivered in a pulsed-format mode of operation that is highly repetitive in time and intensity to provide, for example, relatively precise and predictable cutting. As compared, for example, to a wavelength of 810 microseconds, with other things being equal, the wavelength of 940 microseconds has been determined by the present inventors to have an absorption that is about four times greater for water, two times greater for hemoglobin (for enhanced homeostasis) and about 20% greater for oxyhemoglobin. Alternative wavelengths which can be used according to modified aspects of the present invention can be, for example, 915 microseconds, 960 microseconds and 980 microseconds. Other alternative wavelengths which can be used in other modified aspects of the invention can comprise the mentioned wavelengths, plus or minus about 50 nanometers.

As shown in FIG. 4A, each pulse of the output optical energy waveform 93 can comprise, for example, a pulse duration 96 of about 50 microseconds, a pulse interval 98 of about 450 microseconds, and a pulse period of about 500 microseconds. The magnified view of a pulse featured in FIG. 4B shows that the pulse duration 96 has room for being further reduced in duration. For example, the pulse duration 96 can, according to certain embodiments, be reduced from about 50 microseconds all of the way down to about 10 microseconds. Thus, as illustrated, the output optical energy waveform 93 can comprise a repetition rate of about 2 kHz. The average power output, defined as the power delivered over a predetermined period of time, can be about 1 W. The repetition rate can also be, for example, about 10 kHz, corresponding to a pulse period of about 100 microseconds. The full-width half-max of the pulse may be about 50 to 100 microseconds. In accordance with a typical embodiment, the repetition rate can be varied from about 1 kHz to about 5 kHz, and the average power output can be varied from about 0.5 W to about 1.5 W. In typical embodiments, the pulse length can be varied from about 50 microseconds to about 1000 microseconds, and the pulse interval can be varied from about 100 microseconds to about 2000 microseconds, which parameters may correspond, for example, to pulse repetition rates of about 0.5 kHz to about 5 kHz. The depicted output optical energy waveform 93 thus has a pulse duration 96 and a pulse interval 98 which are both on the order of tens of microseconds. The pulse period is indicated with reference designator number 101 in the depiction of FIG. 4A. FIG. 5 shows an output optical energy waveform 104 comprising, for example, a pulse duration 106 of about 500 microseconds and a pulse interval 110 of about 50 microseconds.

According to the present invention, the system 67 of the current invention can be configured to implement output optical energy waveforms 93 that minimize an impartation of thermal energy into the target tissue (e.g., soft tissue). As an example, the thermal diffusion time, or thermal relaxation time, for highly-absorbing soft tissue is about 150 to 200 microseconds. Thus, according to an aspect of the present invention, for certain applications, the pulse duration of the optical beam (e.g., the output optical energy waveforms 93) can be approximately equal to or less than the thermal relaxation time, which will help to confine or limit the amount of energy dissipation, or the area of thermal affection, of the impingent energy footprint on or within the treatment area. Pulse durations that are longer than the thermal relaxation time can be less efficient and cause the spot to undesirably grow by thermal diffusion. In one implementation, the pulse duration is set to have a value (e.g., 50 microseconds) that is less than the thermal relaxation time. In another implementation, the pulse interval is set to have a value (e.g., 450 microseconds) that is equal to or greater than the thermal relaxation time. Another implementation can comprise a combination of these two aspects, wherein the pulse duration can be set to be below the thermal relaxation time and the pulse interval can be set to be equal to or greater than the thermal relaxation time.

According to another aspect of the present invention, the output optical energy waveform 93 can be varied by way of independent adjustments to one or more of the pulse duration 96 and the pulse interval 98. By way of providing independent adjustments to one or more of the pulse duration 96 and the pulse interval 98, and, preferably, both, the pulse duty cycle, defined as the pulse duration 96 divided by the pulse interval 98, can be controlled. As presently embodied, the pulse duty cycle can be adjusted from, for example, about 5% to about 95%. In particular implementations, it may be varied, for example, from about 10% to about 50%. Thus, the pulse duration can be set, independently of, for example, the pulse interval, to have a value (e.g., 50 microseconds) that is below the thermal relaxation time; the pulse interval can be set, independently of, for example, the pulse duration, to have a value (e.g., 450 microseconds) that is equal to or longer than the thermal relaxation time; and/or the pulse duration and pulse interval can be set to be below, and equal to or greater than, the thermal relaxation time, respectively, to approach or achieve, for example, a characteristic referred to as cold cutting.

Setting of the pulse duration and pulse interval as described in the foregoing paragraph can facilitate a type of cold-cutting tissue interaction. Cold cutting may bring about certain characteristics or advantages, as discussed below, while, on the other hand, non cold-cutting modes, or intermediate modes, may bring about additional characteristics or advantages, a few of which are discussed below.

By controlling one or more of the pulse duration 96 and the pulse interval 98, various procedural properties, such as bleeding, can be controlled. For example, increasing the pulse duration independent of, for example, the pulse repetition rate, can operate to decrease bleeding or increase coagulation, as a result of proving a greater thermic effect to the target. The effect of such a mode (e.g., a thermic effect, which may tend, for example, to augment coagulation) can in some instances create greater scar tissue and/or impede the speed or quality of healing of a target. On the other hand, generating a cooler-cutting (e.g., cold cutting) effect, by, for example, outputting optical energy waveform 93 with a reduced pulse duty cycle (and/or, for example, setting the pulse duration and/or pulse interval below, and/or equal to or greater than, the thermal relaxation time, respectively, as described herein) may enable a treated region to heal better or faster, and/or may facilitate implementation of a procedure with less pain to the patient.

Referring back to FIG. 3, an optical interface can be disposed at a termination of the trunk optical fiber 73 near the distal handpiece end 81, wherein the optical interface can be constructed to provide an optical pathway between the trunk optical fiber 73 and an output fiberoptic 107 of an output tip 108. Thus, as presently embodied, the trunk fiber 73 can extend in an uninterrupted fashion from the system 67 up to and through the handpiece 78, terminating at or near the optical interface, which, in turn, can be located at or near the handpiece distal end 81.

The optical interface can be disposed, for example, within and concealed within the handpiece distal end 81 as illustrated. The output tip 108 can be removable in accordance with an aspect of the present invention. In a number of such embodiments, the handpiece distal end 81 and the output tip 108 can be constructed to interact in such a way as to facilitate convenient and rapid attachment and removal of the output tip 108 to and from the handpiece 78. The output tip 108 can additionally, or alternatively, be removed and interchanged with other output tips in accordance with an aspect of the present invention.

According to another aspect of the current invention, the output tip 108 can additionally, or alternatively, comprise a bendable tip cannula 109. Furthermore, according to yet another aspect of the invention, the output tip 108 can additionally, or alternatively, comprise a disposable output tip 108, which may or may not (according to various, non-interchangeable embodiments) comprise a cannula, which may or may not (according to various, non-interchangeable embodiments) be bendable. In the case of a bendable tip cannula 109, it may comprise a pliable material, such as a pliable metal. According to typical implementations of the bendable tip cannula 109, the bendable tip cannula 109 can be bent at any angle, can have various diameters and lengths, and/or can be packaged, for example, pre-sterilized in a sealed, sterile package.

Regarding such a bendable tip cannula 109, the pliable material may comprise, for example, a treated stainless steel material. The stainless steel material may be treated to make it bendable and/or to make it more readily bendable without kinking Following an exemplary treatment of the bendable tip cannula 109 while, for example, the bendable tip cannula 109 is in a pre-bent orientation (or following treatment of the material used to make the cannula before the cannula is formed), the bendable tip cannula 109 can be bent one or more times while remaining operable. In certain implementations, the bendable tip cannula 109 can be non-destructively bent multiple times at various angles (e.g., 30 degrees, or 45 degrees) up to about 90 degrees from the pre-bent (straight) orientation, at about a 2 or 2.5 mm radius of curvature, without damage to structure or function. A 2 mm radius of curvature may be obtained, for example, by bending the bendable tip cannula around a cylindrical object having a diameter of about 4 mm.

In other implementations, the bendable tip cannula 109 can be non-destructively bent multiple times at various angles up to about 120 degrees from the pre-bent (straight) orientation, at a 2.5 mm radius of curvature, without damage to structure or function of the bendable tip cannula. A 2.5 mm radius of curvature may be obtained, for example, by bending the bendable tip cannula around a cylindrical object having a diameter of about 5 mm.

In further implementations, the bendable tip cannula 109 can be non-destructively bent a relatively large number of times, at any of the referenced angles and radiuses of curvatures, without affect to or attenuation in function. Other embodiments encompass bending the bendable tip cannula 109 a relatively large number of times, at any of the referenced angles and radiuses of curvatures, without compromise to its ability to operate in its normal or intended capability.

According to other implementations, the bendable tip cannula 109 can be bent a relatively large number of times to a maximum angle of about 120 degrees from the pre-bent (straight) orientation, at a radius of curvature of about 2.5 mm, while remaining fully, or in other embodiments substantially, or in other embodiments adequately, operable. In a typical embodiment, the relatively large number can be three, four or five, but in modified embodiments smaller or larger numbers can be implemented. A bendable stainless steel material that may be used to form the bendable tip cannula 109 can be obtained or purchased as a Metric Hypodermic Tube (e.g., Gage Sizes 18, 19 or 20) from New England Small Tube Corporation, of Litchfield, N.H.

Figure 9C:
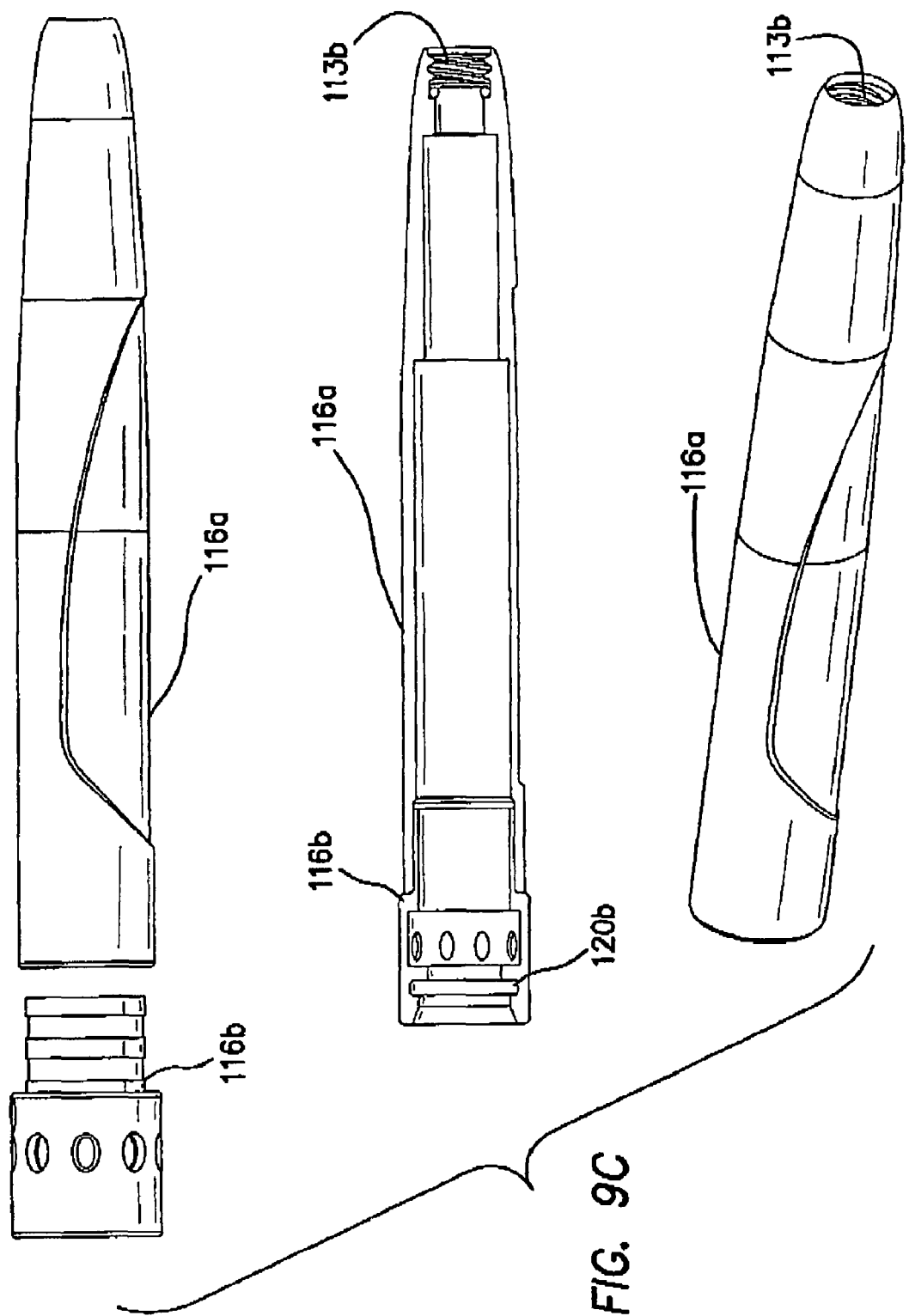
FIG. 9C shows a side-elevation view of the outer layer and coupling member, a cross-sectional view of the outer layer and coupling member, and a perspective view of the outer layer.

A side-elevation view of an exemplary output tip 108, comprising an output fiberoptic 107, a bendable tip cannula 109 and a ferrule 112 with threads 113a, is depicted in FIG. 6. The ferrule 112 may comprise, for example, plastic (e.g., acrylic or polycarbonate) that is, for example, transparent to the laser beam. A cross-sectional view of this output tip 108, secured to the handpiece 78 via, for example, engagement of threads 113a of the output tip 108 with corresponding threads 113b of an outer layer 116a of the handpiece 78, is shown in FIG. 7. FIG. 8A is a side-elevation view of the output tip 108 connected to the handpiece 78, and FIG. 8B is a cross-sectional view of the assembly of FIG. 8A. FIG. 9A shows a side-elevation view of an outer layer 116a of the handpiece 87; FIG. 9B shows a side-elevation view of the outer layer 116a along with a coupling member 116b; and FIG. 9C shows a side-elevation view of the outer layer 116a and coupling member 116b, a cross-sectional view of the outer layer 116a and coupling member 116b, and a perspective view of the outer layer 116a.

As can be discerned from FIGS. 8B, 9B and 10A, the outer layer 116a and coupling member 116b can be secured over an inner assembly 117 including the output tip 108, cf. FIG. 10A, by moving the outer layer 116a and coupling member 116b proximally over the inner assembly 117 (i.e., moving over and around the output tip 108 and progressing proximally to a proximal end of the inner assembly 117). The threads 113a/113b can then be coupled and, further, protuberances 120a of the inner assembly 117 can be disposed within a recessed area 120b of the outer layer 116a. Release buttons 121 can be pressed by a hand of a user to release the protuberences 120a from within the recessed area 120b to facilitate removal of the inner assembly 117 from within the outer layer 116a and coupling member 116b.

Figure 11:
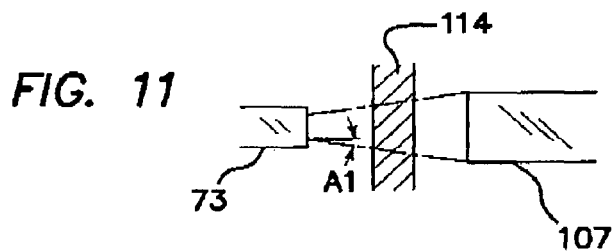
FIG. 11 is a schematic representation of the portion depicted in FIG. 10.
Figure 10:
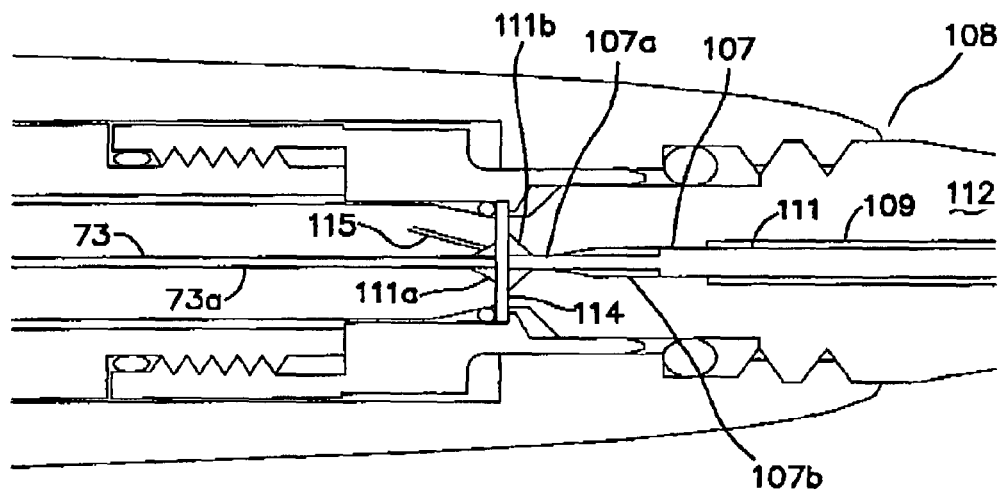
FIG. 10 is a magnified view of portions of the structure of FIG. 8B.

FIG. 10 is a magnified view of portions of the structure of FIG. 8B, and FIG. 10A is a perspective view of portions of the structure of FIG. 8B. The perspective view of FIG. 10A depicts the inner assembly 117 including the output tip 108. FIG. 10B is an exploded, perspective view of the assembly of FIG. 10A, and FIG. 10C is a partially-assembled view of the components depicted in FIG. 10B. FIG. 11 is a schematic representation of the portion depicted in FIG. 10.

Figure 12:
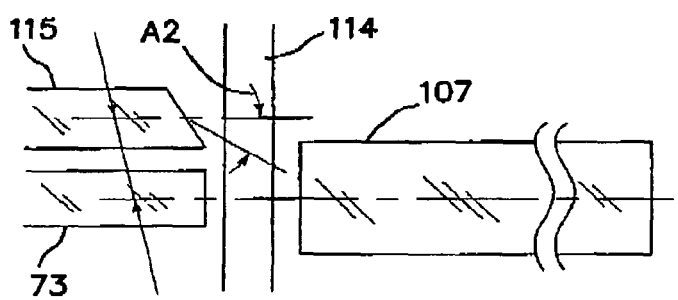
FIG. 12 is a schematic representation of the portion depicted in FIG. 10 according to a modified embodiment.

As elucidated in FIG. 10, the optical interface can comprise, for example, a physical barrier that is optically transparent, such as a window 114 shown in FIGS. 10-12. An O-ring 118 can be used to facilitate positioning and/or stabilization of the window 114. Additionally, or alternatively, one or more of the ferrule 112 and a similarly-shaped (e.g., of similar or the same material) ferrule 119 can function to contact one or more corresponding sides of the window 114. The window 114 can be readily removable and field replaceable using an attachment scheme that does not rely on adhesives or permanent formations, wherein removal of the output tip 108, ferrule 112, and/or additional components can provide access to the window 114 for removal or insertion thereof. Although modified implementations of the optical interface may comprise lenses or other optical elements on one or both sides (e.g., proximal and distal sides) of the optical interface, the illustrated embodiment comprises neither. According to this illustrated implementation and aspect of the invention, lens structure or functionality is not provided on either side of the window 114 to attenuate a risk of, for example, misalignment, leaking, and/or damage when the output tip 108 is inserted, removed or otherwise repositioned.

As can be seen from a review of FIGS. 10 and 11, each of the trunk optical fiber 73, which is shown in FIG. 10 disposed within a channel 73a, and the output fiberoptic 107, which is shown in FIG. 10 comprising a glass fiber 107a encompassed within a jacket 107b (e.g., a Teflon or polyethylene jacket), can be spaced from a corresponding surface of the window 114. In the illustrated implementation, each of the trunk optical fiber 73 and the output fiberoptic 107 can be spaced about 100 microns from a corresponding surface of the window 114. A point on the perimeter of the distal end (i.e., output surface) of the trunk optical fiber 73 can be referred to as a beginning point. Referring to FIG. 11, an angle of divergence A1, measured between the optical axis of the trunk optical fiber 73 and a path of output energy extending from the beginning point to an edge (i.e., perimeter edge) of the proximal end of the output fiberoptic 107, can be about eight degrees. Although the proximal input end of the output fiberoptic 107 does not contact the window 114, intermediate or outer portions of the ferrule 112 do, as can be seen in FIG. 10, to thereby ensure exact positioning of the output tip 108 with each insertion of each output tip 108. In a modified embodiment, a push/twist/lock design, or a click or snap design, can be implemented instead of the illustrated threaded design for securing the output tip 108 to the handpiece 78.

In the depictions of, for example, FIGS. 7 and 10, an air gap 111 is disposed between the output fiberoptic 107 and the bendable tip cannula 109. FIG. 7 shows an embodiment wherein an aiming beam fiber 115 delivers radiation to the optical interface (e.g., window 114) at a an angle or at a relatively steep angle (e.g., up to about 30 degrees, or up to about 45 degrees, or up to about 60 degrees, compared to the trunk optical fiber 73 axis), and further depicts another (e.g., alternative) embodiment wherein the aiming beam 115a delivers radiation to the optical interface 114 along an axis that is substantially parallel to the trunk optical fiber 73. Furthermore, in the illustrated embodiments of, for example, FIGS. 7 and 10, an air gap 111a is disposed between the distal end of the aiming beam fiber 115 (or 115a) and the proximal side of the window 114 and is further disposed between the distal end of the trunk optical fiber 73 and the proximal side of the window 114. Moreover, in this illustrated embodiment, another air gap 111b is disposed between the distal side of the window 114 and the proximal end of the output fiberoptic 107.

Figure 13:
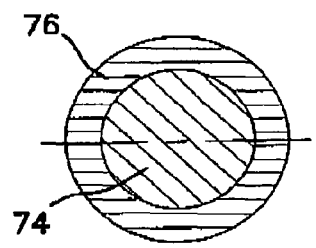
FIG. 13 depicts an irradiation pattern that may be generated and output from the embodiment of FIG. 12.

FIG. 12 is a schematic representation of the portion depicted in FIG. 10 according to a modified embodiment, and FIG. 13 depicts an irradiation pattern that may be generated and output from the modified embodiment of FIG. 12. In this embodiment, instead of the aiming beam fiber 115 being configured to deliver radiation to the optical interface (e.g., window 114) at a relatively steep angle as shown in FIG. 10, the aiming beam fiber 115 can be constructed to deliver radiation to the optical interface along a path that is substantially parallel to the trunk optical fiber 73. In either implementation, aiming-beam light striking window 114 inherently results in a portion of that light being deflected (e.g., leaking) into the ferrule 112. Now, when the ferrule 112 is formed of a material transparent to the laser beam, as mentioned above, the aiming-beam light (comprising visible light) within the ferrule 112 can be seen by a user, resulting in an appearance of the ferrule 112 glowing with, for example, the color of the aiming beam light. According to one aspect of the present invention, introducing disturbances or other light deflecting structures or compositions within the ferrule 112 and/or on the surface of the ferrule 112 (and/or increasing or altering the amount or angle, or, potentially, other aspects or characteristics) of aiming-beam light entering the ferrule 112 can alter (e.g., enhance, augment, or dramatically enhance) the glowing appearance of the ferrule 112. For instance, the ferrule 112 may be constructed to have different degrees of transparency and/or different colors wherein ferrules (of replaceable output tips) can be formed to have increasing levels of transparency and/or different colors. In FIG. 12F, the top, bottom-right and bottom-left ferrules can be formed, for example, to have a blue tint, a yellow tint and no tint, respectively.

Furthermore, when another portion of the aiming-beam light is directed into the glass fiber 107a, as discussed previously, this other portion of light travels to the distal, output end of the glass fiber 107a and can be seen by a user, resulting in an appearance of the distal, output end of the output fiberoptic 107 (e.g., the exposed glass fiber 107a) glowing with the color of the aiming beam light. According to an aspect of the present invention, introducing surface disturbances or other alterations in structure or material within or on the surface of the distal, output end of the glass fiber 107a can alter (e.g., enhance, augment, or dramatically enhance) the glowing appearance of the distal, output end of the glass fiber 107a. For instance, the glass fiber 107a may be constructed to have different degrees of transparency and/or different colors. In a typical embodiment, however, the glass fiber 107a is formed of a material that is entirely or substantially completely transparent to the cutting-beam wavelength (e.g., 940 nm).

As presently embodied, the jacket 107b can be constructed, for example, to be transparent or semi-transparent, to thereby exhibit a glowing appearance corresponding to the color of the aiming beam light. According to an aspect of the present invention, introducing surface disturbances or other alterations in structure or material within or on the surface of the jacket 107b can alter (e.g., enhance, augment, or dramatically enhance) the glowing appearance of the jacket 107b. As an example, the jacket 107b may be constructed to have different degrees of transparency and/or different colors.

In any of the preceding embodiments, the color, brightness or other parameter of the aiming beam may be varied to provide a different visual effect. Typically, the aiming beam can have a red color, and this can be used with ferrules having clear transparencies (corresponding, for example, to a color and transparency of water) or transparencies with slight hues of one or more colors, such as, for example, a transparent yellow ferrule).

FIGS. 12A, 12B, 12C and 12D show perspective, lengthwise cross-sectional, front-end, and transverse cross-sectional views of components (including ferrule 112) corresponding to the embodiment of FIG. 12.

Figure 12A:
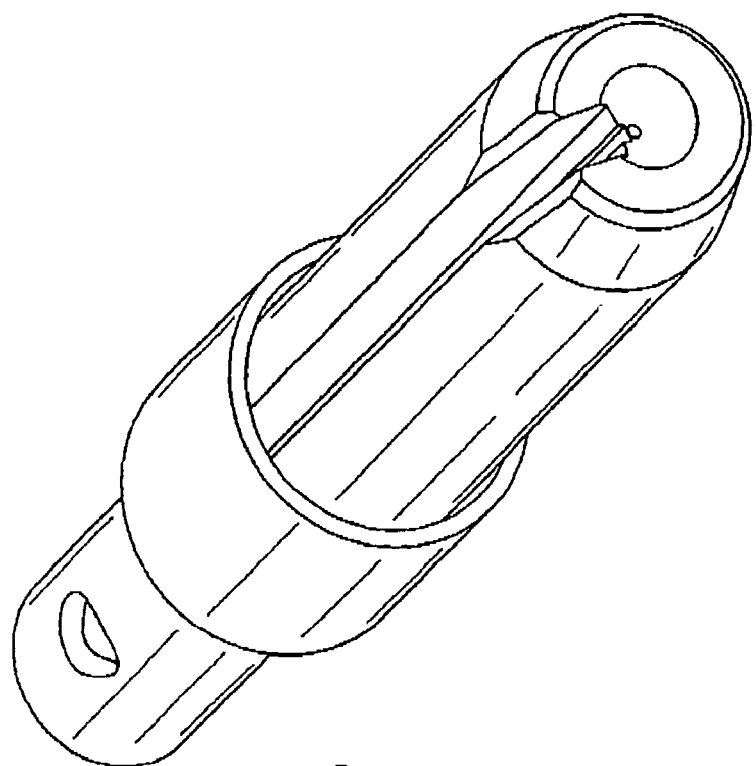
FIGS. 12A, 12B, 12C and 12D show perspective, lengthwise cross-sectional, front-end, and transverse cross-sectional views of components including a ferrule 112 corresponding to the representation of FIG. 12.
Figure 12B:
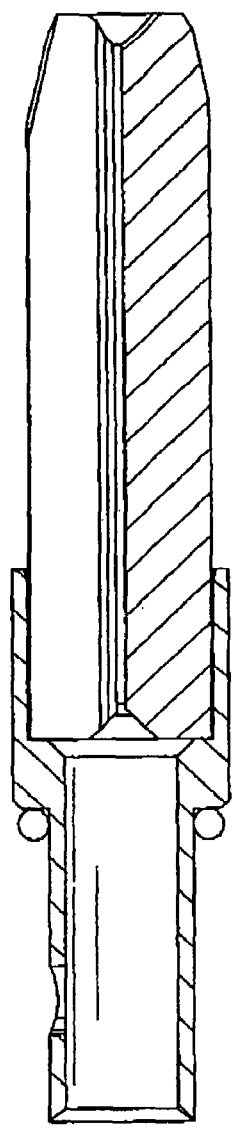
Figure 12C:
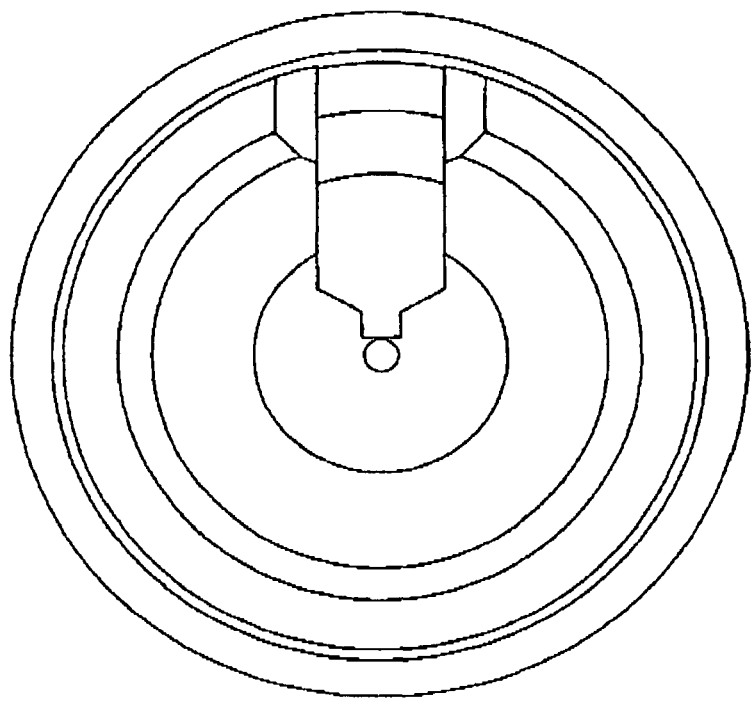
Figure 12D:
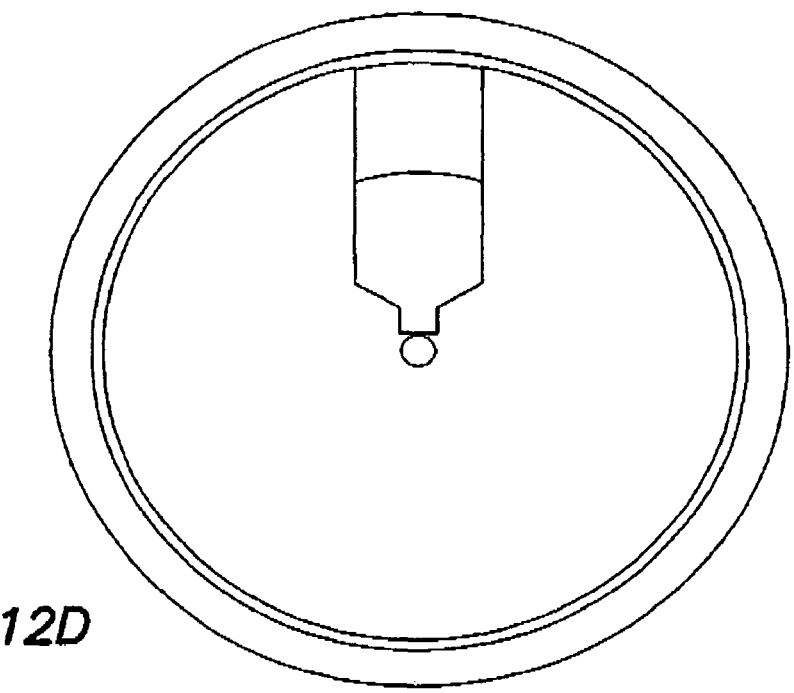
Figure 12E:
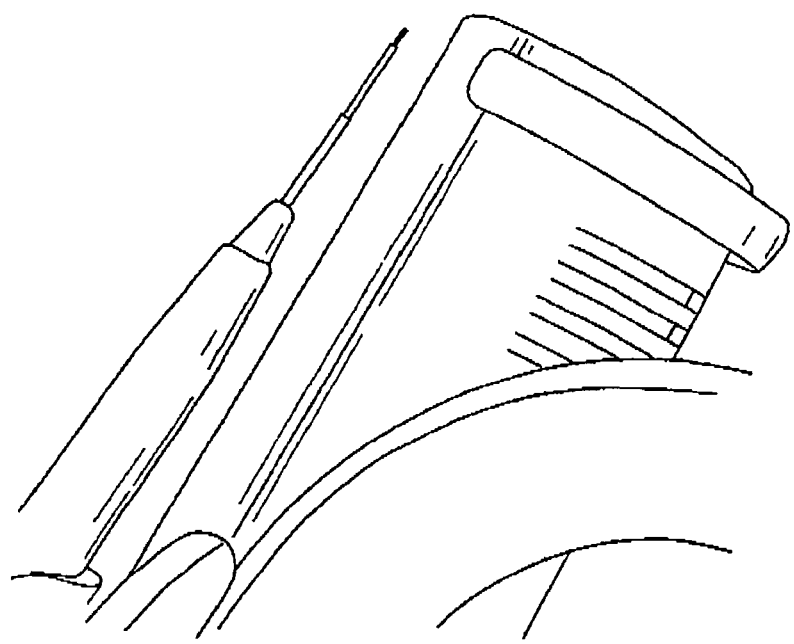
FIGS. 12E and 12F show side-elevation views of components including a ferrule and an output fiberoptic 107.
Figure 12G:
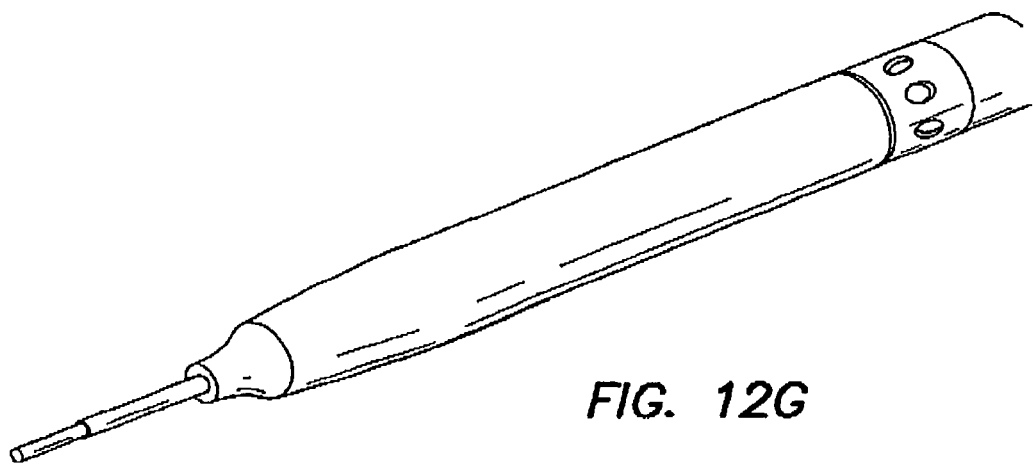
FIG. 12G shows a perspective view of components including a ferrule and an output fiberoptic 107, with an aiming beam in an "on" state so that exposed parts of the output fiberoptic and ferrule glow.
Figure 12F:
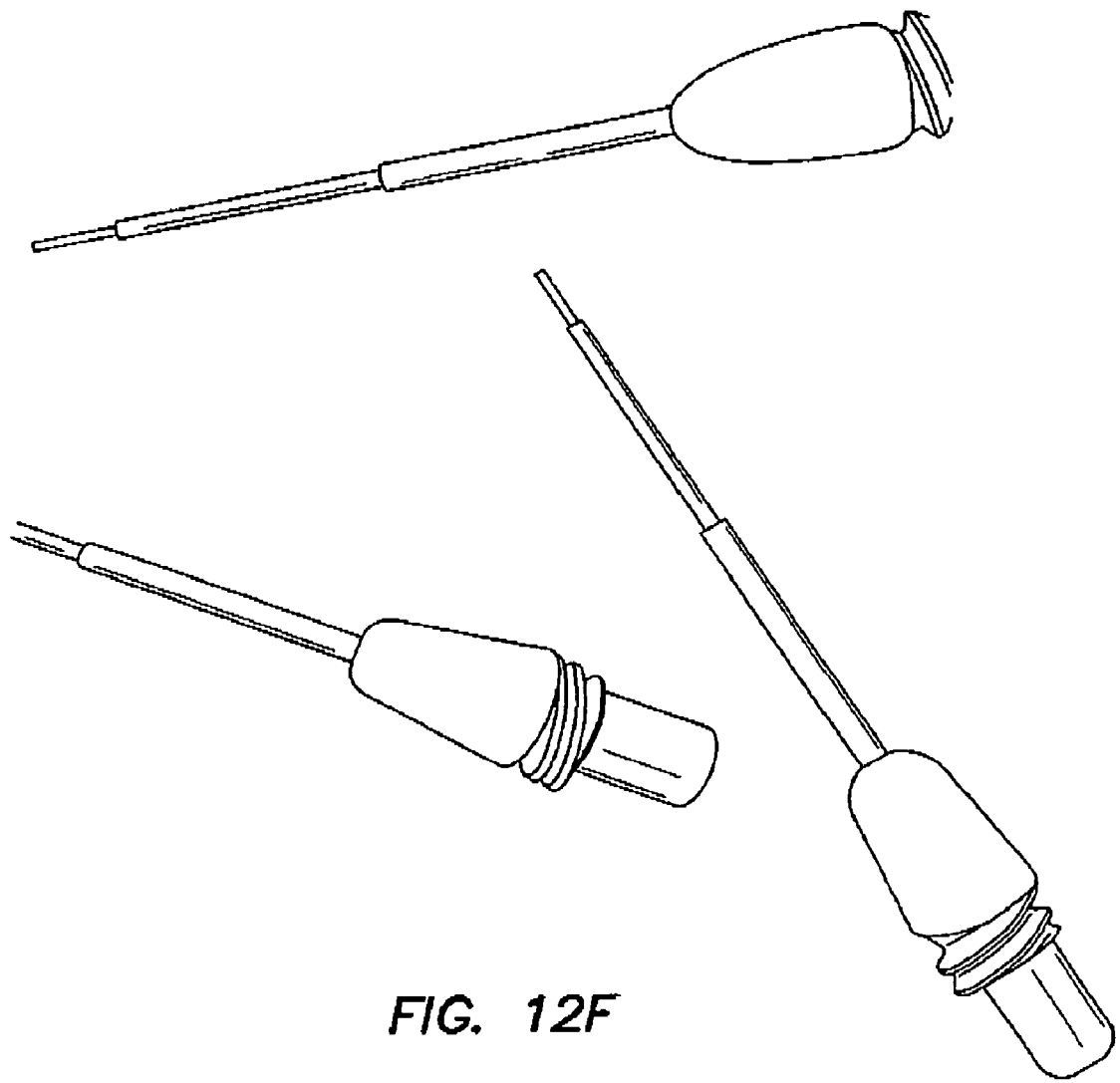

FIGS. 12E and 12F show side-elevation views of components (including ferrule 112 and output fiberoptic 107), and FIG. 12G shows a perspective view of components (including ferrule 112 and output fiberoptic 107) but with the aiming beam "on" so that exposed parts of the output fiberoptic and ferrule glow. According to one aspect of the present invention, the material of the ferrule can have a transparency of at least about 50%. According to another aspect, a transparency of the material of the ferrule can be selected to be sufficient to allow a human naked eye to see (e.g., clearly see) the bendable cannula 109 within the ferrule (c.f., lower-left fiberoptic of FIG. 12F).

The material of the ferrule 112, when formed into a planar sheet with smooth surfaces and a thickness of about 5 mm, can have a 50% transparency, meaning, as used herein, that it will transmit about 50% of light from the cutting-beam laser (e.g., laser light having a wavelength of 940 microns). This transparency may be altered, such as, for example, increased to any value up to a 100% transparency. A transparency of the non-tinted ferrule of the lower-left replaceable output tip 108 shown in FIG. 12F can be (e.g., is) about 80% to 90%.

In a particular embodiment, about 85% of the cutting-beam laser light exiting from the window 114 enters into the output fiberoptic 107 and about 8% of it enters into the ferrule 112. Within the ferrule, about half of it is absorbed and about half passes through.

Regarding the aiming beam, in a particular embodiment, about 50% of the aiming beam exiting from the window 114 enters into the output fiberoptic 107 (cf. bottom-right depiction of FIG. 12H) and about 50% of it enters into the ferrule 112. In one embodiment, within the ferrule, a percentage (e.g., about half) of it is absorbed and another percentage (e.g., about half) passes through, to create a glowing effect.

Figure 12H:
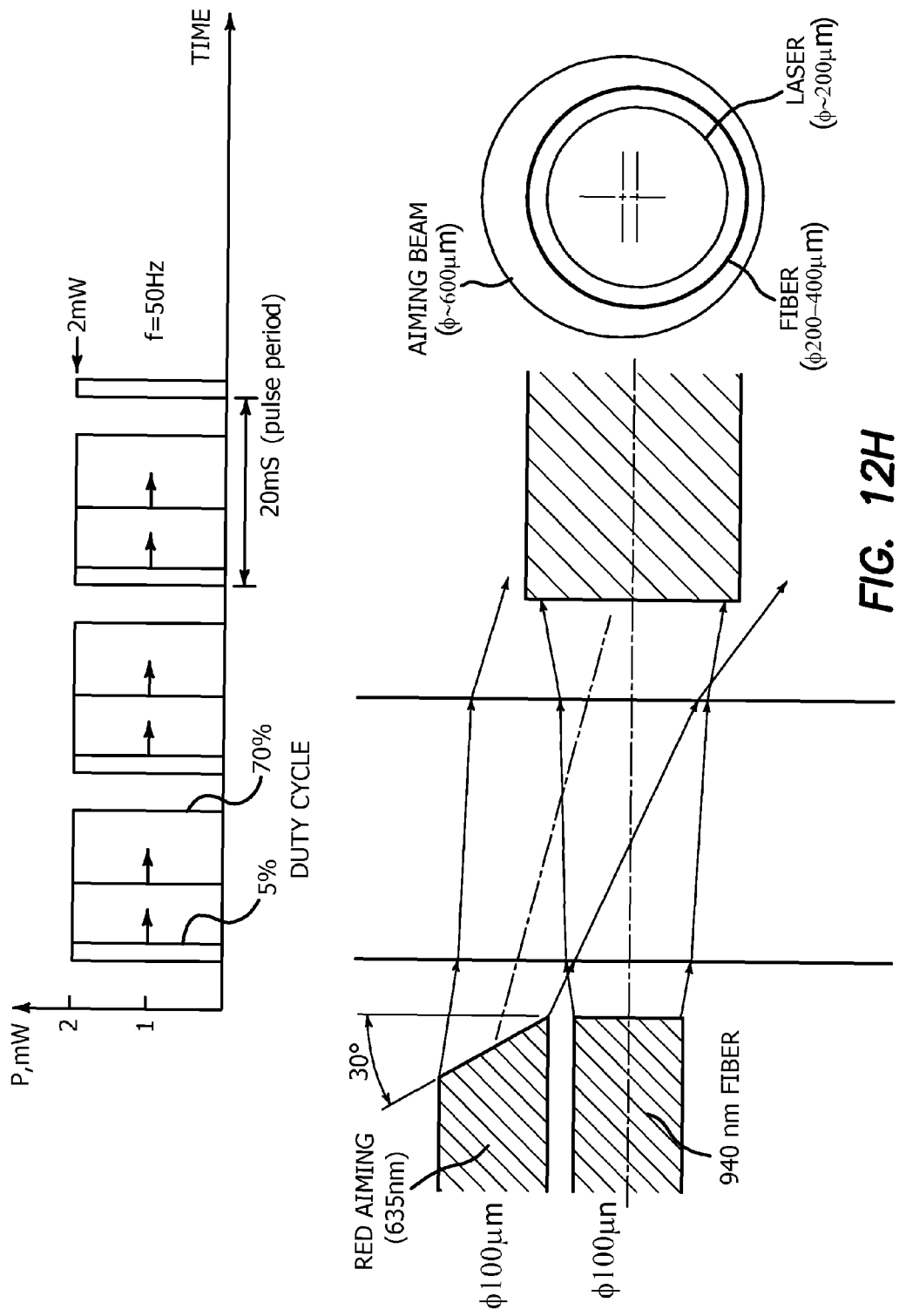
FIG. 12H provides schematic representations of aiming-beam characteristics, of a portion of structure depicted in FIG. 10, and of laser and aiming-beam spots projected onto the input end of an output fiberoptic.

With reference to FIG. 12H, the solid cross-hairs at the center of the output fiberoptic (fiber) indicate an optical center thereof. These solid cross-hairs also correspond to an optical center of the cutting-beam radiation (laser) that is projected onto the input end of output fiberoptic. The phantom cross-hairs indicate an optical center of the aiming-beam radiation (aiming beam) that is projected onto the output fiberoptic. It can be discerned from the figure, in accordance with an aspect of the invention, that the projection of aiming-beam radiation is not centered on the output fiberoptic, as a consequence of the depicted circles not being concentric and the cross-hairs having different positions. In modified embodiments, the spot size, optical center as projected onto the output fiberoptic, and/or angle of incidence onto the output fiberoptic, of the aiming beam may be varied to introduce more or less aiming-beam light into the ferrule and/or into the output fiberoptic.

The aiming beam can comprise a wavelength of about 635 nm and, as it exits the window 114, can have a power of about 1 to 3 mW and a spot size of about 600 microns. As indicated in FIG. 12 and in the lower-left depiction of FIG. 12H, the aiming beam can be configured and routed to impinge on the output fiberoptic 107 at an angle, such as at an angle of about 15 degrees with respect to an optical axis of the output fiberoptic. The aiming beam may comprise one or more of continuous wave (CW) and modulated energy.

According to an aspect of the present invention, the aiming beam can be operated in a modulated mode at lower output (e.g., brightness) settings and a CW mode at higher output (e.g., brightness) settings. As an exemplary embodiment, the aiming beam when modulated may comprise (1) a modulation frequency of about 50 Hz corresponding to a pulse period of about 20 ms, (2) a peak power of about 2 mW, and (3) a pulse duty cycle, defined as the pulse duration divided by the pulse interval, ranging from about 5% to about 70%. A particular implementation may comprise first, second, third and forth presets that output an aiming beam, with any one or more of the above-mentioned aiming beam parameters, with pulse duty cycles of 5, 10, 30 and 70, respectively, and may further comprise a fifth preset that outputs an aiming beam, with one or more of the above-mentioned aiming beam parameters, in a CW mode.

Another aspect of the present invention introduces structure and/or algorithms for altering a visual, structural, or functional characteristic of one or more of the ferrule 112, output fiberoptic 107, or any other component described herein (e.g., the display), to thereby provide an indication to the user, following a predetermined number of uses or amount of time of use of the output fiberoptic 107. The indication communicates to the user that the output fiberoptic 107 (e.g., the entire replaceable output tip 108) should be replaced. Feedback light can used to detect a change in feedback beam quality corresponding to a degradation (e.g., fraying) of a distal-most output end of the output fiberoptic 107, the detection of which can trigger an occurrence of the indication. The indication can also be triggered by the occurrence of an autoclave procedure (for a single use limitation) or of a predetermined number of autoclave procedures (for a multiple-use limitation), after which the output fiberoptic tip 107 should be replaced wherein an adhesive used in the output fiberoptic 107 can be selected to degrade or disintegrate when subjected to the autoclave procedure or procedures. In another implementation, the ferrule 112 can comprise a material that changes color after a predetermined amount of use time has occurred, thus providing the indication.

The output surface of the aiming beam fiber 115 can be truncated and polished at a non-normal angle so that the output surface directs the aiming beam into the center of the output fiberoptic 107. A point on the output surface of the aiming beam fiber 115 intersected by the optical axis of the aiming beam fiber 115 can be referred to as an output point. With reference to FIG. 12, the angle A2 between the optical axis of the aiming beam fiber 115 and a path of output energy directed from the output point into the center of the output fiberoptic 107 may, for example, be from about 10 to 20 degrees in an implementation wherein the center-to-center separation between the trunk optical fiber 73 and the aiming beam fiber is about 130 to 150 microns and the distance from the output end of the trunk optical fiber 73 to the input end of the output fiberoptic 107 is about 300 to 700 microns. With regard to the illumination pattern shown in FIG. 13, a center 74 of the ring is filled with irradiation from the trunk optical fiber 73, and the ring pattern 76 corresponds to radiation from the aiming beam fiber 115. With this irradiation pattern, a quality of the ring pattern can be used to determine a quality of the beam or beams.

A core diameter of the trunk optical fiber 73 can be, for example, about 105 microns, and a core diameter of the output fiberoptic 107 can be, for example, about 200, 300 or 400 microns. As embodied herein, the window 114 can comprise sapphire with an anti-reflective coating (ARC) on one or both of its sides. In a particular implementation, it can comprise a thickness of about 250 microns and a diameter of about 2.5 mm, and can have an ARC disposed on both of its circular surfaces. Other structures and materials may be implemented in modified embodiments, and, according to certain aspects, such modifications can maintain a functionality of the optical interface of providing a thermal and/or thermal barrier while providing an optical pathway between the trunk optical fiber 73 and the output fiberoptic 107. For example, a function of the optical interface can be to dissipate heat to protect the trunk optical fiber 73 output end from damage.

FIG. 14 provides examples of a number of typical bendable tip cannulas, comprising ferrules, which may comprise different colors to indicate different characteristics, and which may be interchangeably affixed to the handpiece 78.

As with typical prior-art implementations, the distal energy output end of the output fiberoptic 107 can exhibit signs of wear or damage after use (e.g., after about 5 minutes of actual lasing time), and thus should be replaced on a frequent and regular basis. The replaceable output tip 108 of the present invention can render such replacements rapid, reliable, efficient, sterile, and convenient. A typical cannula of the invention, such as a typical bendable tip cannula 109, may comprise a one millimeter OD, a 0.1 millimeter wall thickness, and a 2.5 centimeter length, with an inner lumen of the cannula accommodating an output fiberoptic having, for example, a 400 micron diameter, whereby a length of the output fiberoptic protruding distally from the cannula may be, for example, about four to nine millimeters.

Figure 15:
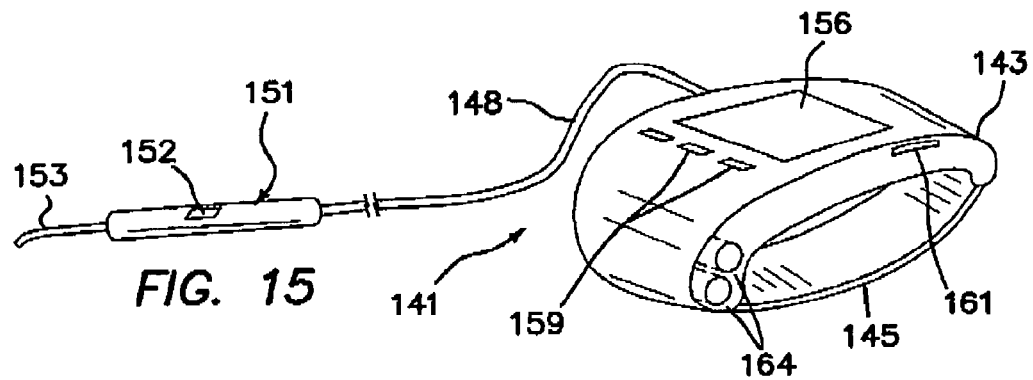
FIG. 15 depicts a body-mount implementation of an electromagnetic energy output device according to an aspect of the present invention.

With reference to FIG. 15, an electromagnetic energy output device is exemplified in the form of a body-mount implementation. The body-attachment (e.g., wrist mount) implementation of the electromagnetic energy output device 141 can comprise a housing 143 with a body attachment (e.g., a wrist band) 145, a fiber optic 148, and an output configuration. The housing can comprise, for example, a display, such as a touchscreen 156, inputs or controls 159, an electromagnetic energy source such as a laser 161, and batteries 164 which may comprise two sets of batteries. The output configuration is embodied in this example as a handpiece 151 with an actuator control 152 for controlling, for example, an on/off state of an electromagnetic energy source (e.g., laser) and with a fiber optic tip 153.

Figure 19:
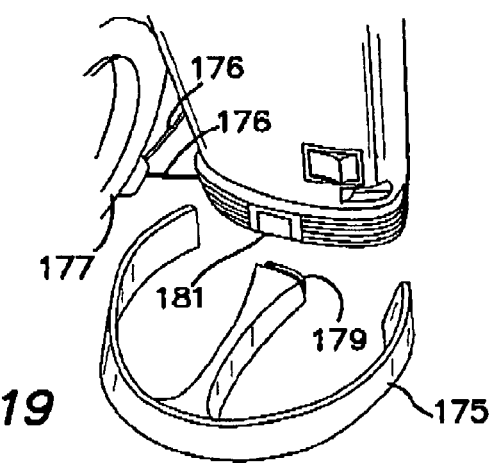
FIG. 19 shows the electromagnetic energy output device of FIGS. 16 and 17 with a detached base according to an aspect of the present invention.
Figure 16:
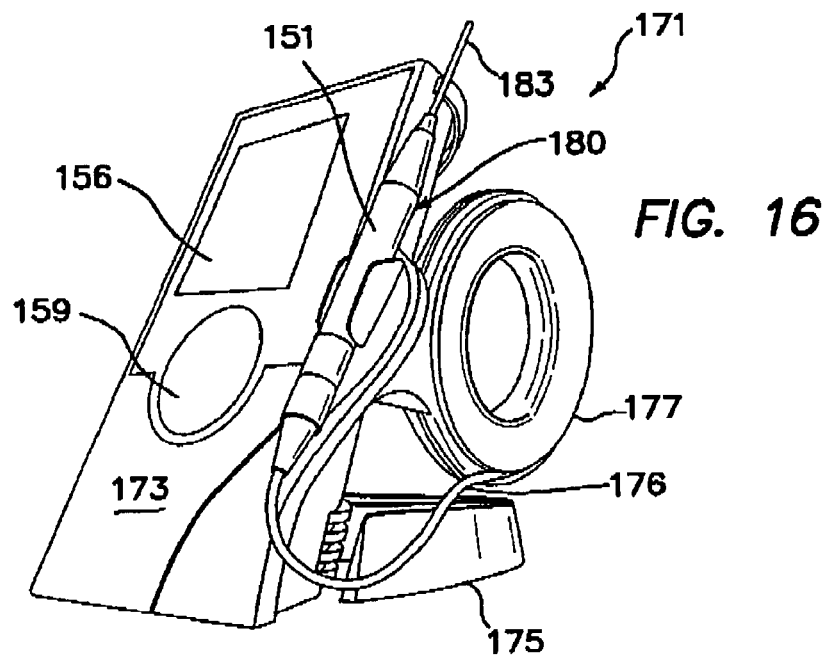
FIGS. 16 and 17 are perspective front and rear views, according to an aspect of the present invention, of an electromagnetic energy output device in the form of a compact, portable assembly that can be carried or mounted with relative ease by a user.
Figure 17:
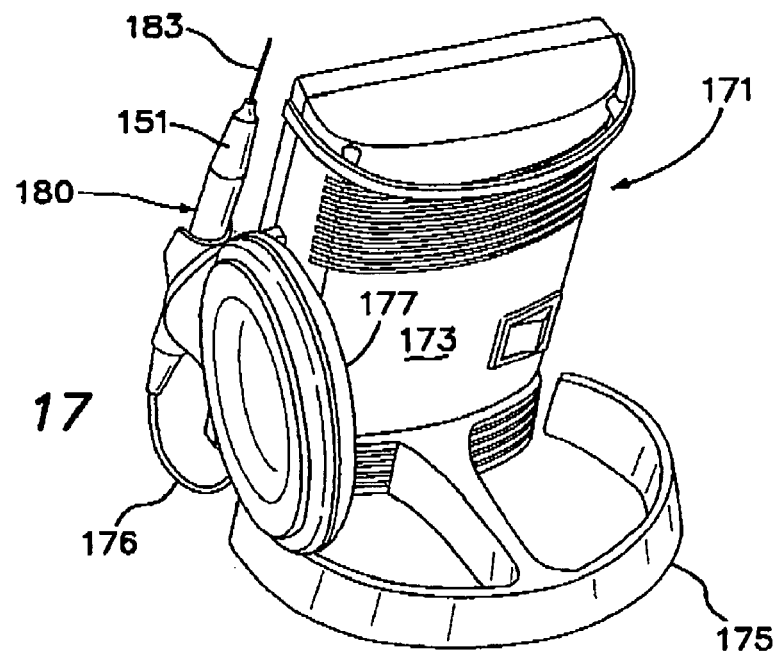

FIGS. 16 and 17 show perspective front and rear views of an electromagnetic energy output device 171 in the form of a compact, portable assembly that can be carried or mounted with relative ease by a user. The electromagnetic energy output device 171 can comprise a housing 173 with a removable base 175 and a removable spool 177. The removable base 175 can be detachably secured to the housing 173 using any known means for providing a removable affixation, such as, referring to FIG. 19, a protuberance or rib 179 of the base 175 constructed to slidably fit into a slot or channel 181 of the housing 173. In operation, a user can lift the housing 173 above the removable base 175 so that the channel 181 is positioned above the rib 179, as exemplified in FIG. 19. Subsequently, the user the user can lower the housing 173 in such a way that the channel 181 contacts, is moved around, and envelops at least a part of the rib 179, until the housing 173 is positioned on the same plane (e.g., table top) on which the removable base 175 rests.

According to the embodiment of FIGS. 16 and 17, the electromagnetic energy output device 171 further comprises a fiber optic 176, which extends from a point of the housing 173 to the removable spool 177 and which further extends to an output configuration 180. The output configuration 180 is embodied in this example as a handpiece 151 having an actuator control (not shown) for controlling, for example, an on/off state of an electromagnetic energy source (e.g., laser) and further having an output fiberoptic which in the illustrated embodiment comprises a replaceable output tip 183. A foot switch can be used in lieu of the actuator for turning the laser on and off, and it can communicate with the housing 173 using a wireless communication protocol, such as Bluetooth® technology.

Figure 18:
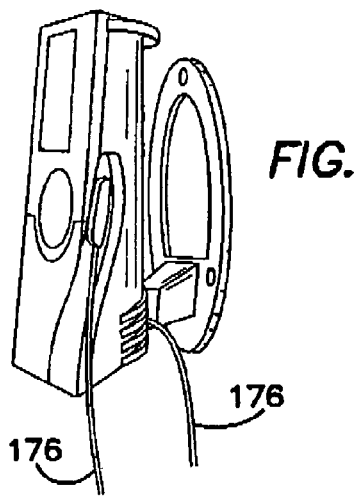
FIG. 18 shows the electromagnetic energy output device of FIGS. 16 and 17 in a wall-mount configuration according to an aspect of the present invention.
Figure 20A:
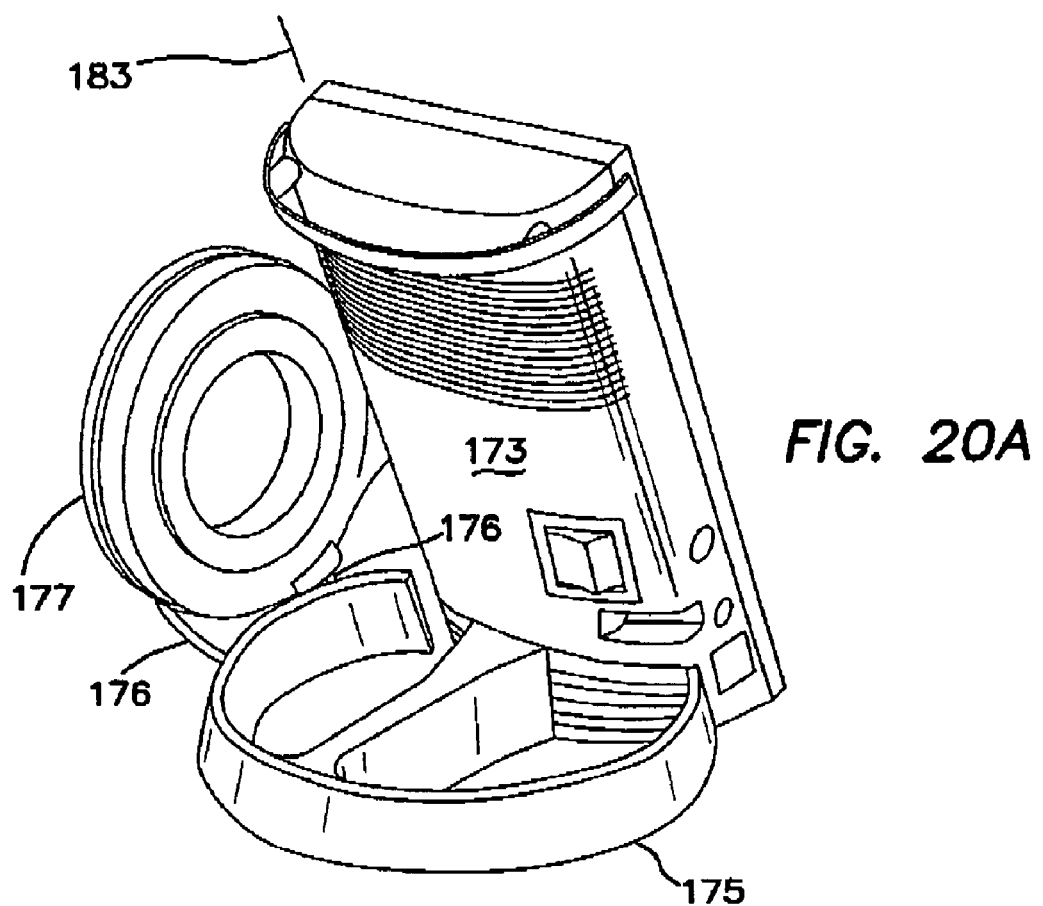
FIG. 20A shows the electromagnetic energy output device of FIGS. 16 and 17, disposed on a flat surface such as a table top according to an aspect of the present invention.
Figure 20B:
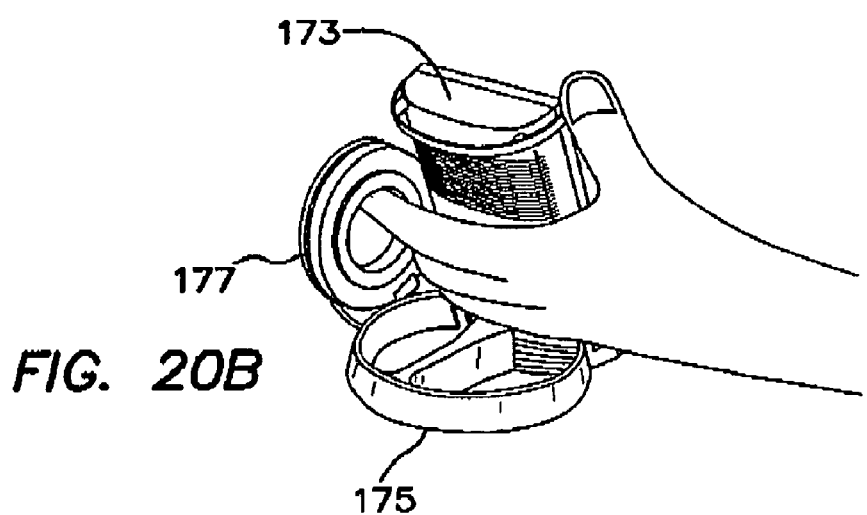
FIG. 20B is a rear view of the electromagnetic energy output device of FIGS. 16 and 17, held by a hand of a user according to another aspect of the present invention.

The electromagnetic energy output device 141 can be hand-held as can be seen with reference to FIG. 20B. The electromagnetic energy output device 141 can also be wall or pole mounted as shown in FIG. 18, or positioned on a table top as elucidated, for example, in FIGS. 16, 17, 19 and 20A.

Figure 21:
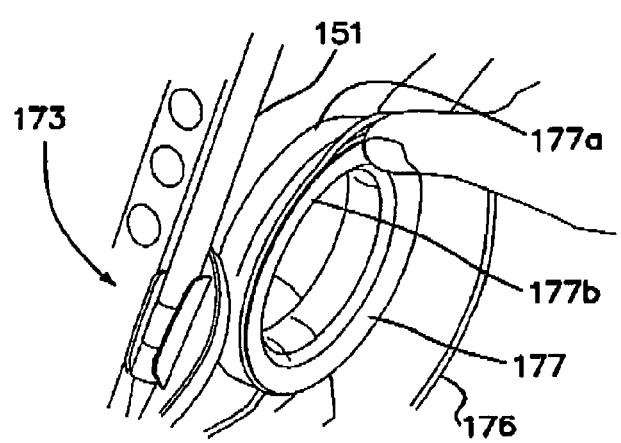
FIGS. 21, 22, 23, 24, 25A and 25B depict various perspective views of spool structures and associated techniques corresponding to aspects of the present invention.
Figure 22:
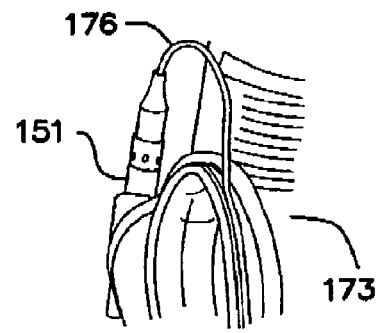

The housing 173 can comprise, for example, a display, such as a touchscreen 156, inputs or controls 159, an electromagnetic energy source such as a laser (not shown), and batteries (not shown) which may comprise two sets of batteries. The electromagnetic energy source can be disposed in a lower, rear portion of the housing 173. A power chord can be implemented as an alternative, or in addition to, the batteries. In a modified embodiment, one or more of a size, shape and capacity of the removable base 175 may be altered or enhanced to form an altered or enhanced removable base 175. An example of an altered base, such as discussed below and shown in FIGS. 26A and 26B, may be formed and implemented for carrying the laser and/or one or more additional, optional lasers. As shown in FIGS. 21, 22, and others, when the removable spool 177 is disposed (e.g., attached) in close proximity to the housing 173, an extra length (e.g., one foot) of fiber optic 176 can be stored in a trip-free (e.g., of reduced clutter) and organized fashion. In modified embodiments, the removable spool 177 can be secured to (and, in other modified embodiments, secured and concealed, for example, within) the housing 173), to thereby provide a technician or user with a means of increasing a length of the fiber optic 176 by advancing additional fiber optic 176 from the removable spool 177 toward the handpiece 151 should the need arise. In a modified embodiment, the removable spool 177 can be disposed, but not necessarily attached, outside of the housing 173 and/or in a vicinity of (e.g., adjacent to or inside of) the handpiece 151. Using this technique, a fiber optic 176 length of, for example, 5 to 8 feet can be maintained in the event of damage, such as an overheating occurrence of the optical interface.

In accordance with an aspect of the current invention, the functionality provided by the disclosed arrangement can be accomplished without the necessity of having the fiber optic 176 slidably disposed within the bendable tip cannula 109. Accordingly, and in contrast to the prior-art construction of FIG. 1, the output fiberoptic 107 can be permanently affixed, such as by an adhesive, within the bendable tip cannula 109.

Figure 26A:
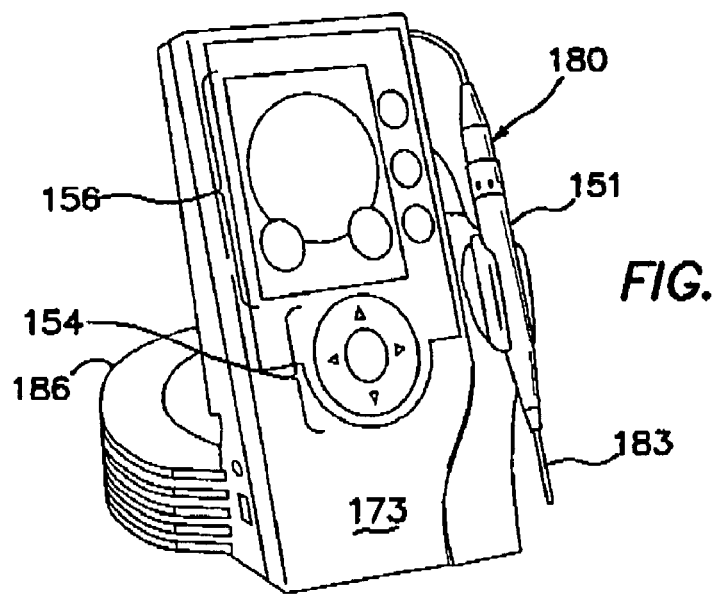
FIGS. 26A-26B depict front and rear perspective views of a modified-base implementation according to an aspect of the present invention.
Figure 26B:
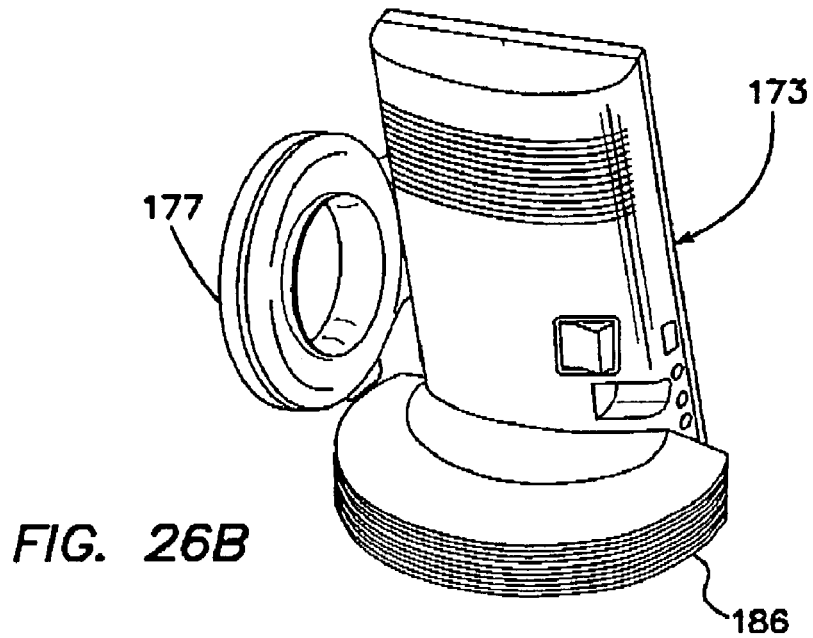

FIG. 26A depicts a particular implementation of a touchscreen and inputs or controls, wherein, for example, the center (e.g., 19.50w) display has left-facing and right-facing arrows for increasing and decreasing various parameters; here power is shown and the dark shaded part on the hemispherical dial shows graphically the degree of that setting compared to the maximum value (cf. a speedometer). An Energy Start display can show how much energy has been delivered total, and can be reset to zero after each use. The Energy Start feature does not have a cap and counts the energy delivered. An Energy Total feature, on the other hand, can count down from a preset total amount to be delivered.

The Energy Total display can be programmed (or chosen from a preset) to specify a total amount of energy (e.g., deliver in one periodontal pocket 5-10 J; for example, it may take 10-15 seconds and typically will be one continuous shot, to be delivered). If too much energy is delivered, for example, overheating and/or removal of too much tissue may occur; the user typically cannot see within the periodontal pocket, for example, and, furthermore, the patient may not be able to feel the pain in an overdose situation.

Average Power can be calculated in real-time and displayed in J/s. While the figures depict a touchscreen, the functionality of the current system can also be obtained using the user-interface inputs at the bottom of the unit comprising an Enter input and four arrow inputs. The depicted assembly can be wall mounted, wrist mounted (e.g., with a battery, with fewer hard (physical) buttons and more of a display/software driven user interface, and shorter cables/fibers) as exemplified in the depiction and discussion regarding FIG. 15, or belt mounted.

Figure 23:
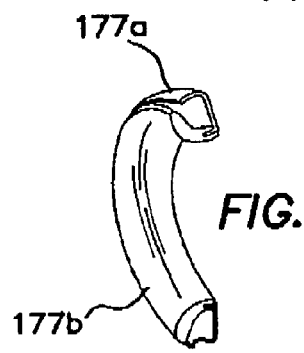
Figure 24:
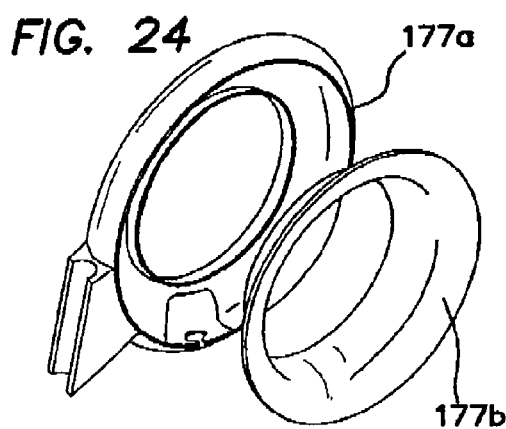
Figure 25A:
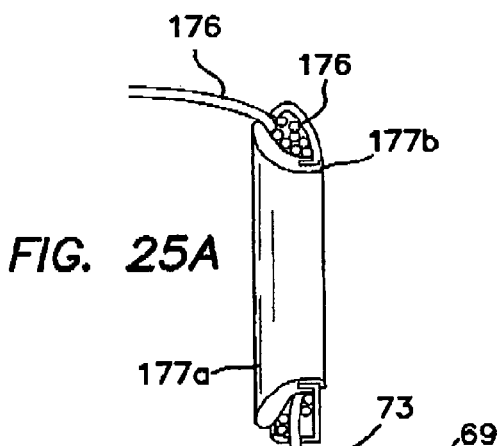
Figure 25B:
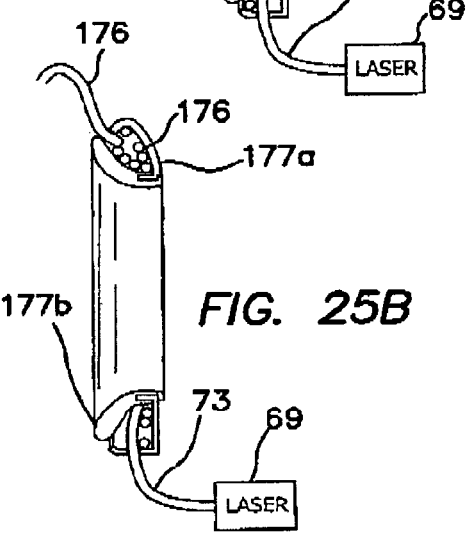

The removable spool 177 can comprise, for example, two parts, as shown in FIGS. 23 and 24, to provide storage and protection to the fiber optic 176. In the exemplary implementation shown in FIGS. 21-25B, the removable spool 177 comprises a spool enclosure 177A and a rubber enclosure 177B. The rubber enclosure 177B can comprise a rubber hub, as depicted, which clips onto the spool enclosure 177A and which controls winding and unwinding of the fiber optic 176. A domed interior of the spool enclosure 177A allows coils of the fiber optic 176 to expand in the chamber. With reference to FIG. 24, in certain implementations fiber optic 176 which is wrapped around the removable spool 177 is unspooled and released as a user pulls the handpiece away from the removable spool 177. Referring to FIG. 25A, during winding, the rubber enclosure 177B (e.g., rubber hub) directs windings of the fiber optic 176 inward and supplies containment pressure. Referring to FIG. 25B, it can be seen that, during unspooling, pulling of optical fiber 176 out of the spool causes the rubber enclosure 177B (e.g., rubber hub) to deflect away from the spool enclosure 177A, allowing the fiber optic 176 within the removable spool 177 to spill out automatically so that the user does not need to manually unwind the fiber optic 176 from the removable spool 177.

The laser module 69 of, for example, FIGS. 25A and 25B, can comprise a diode laser. The diode laser of the system can be disposed near the bottom of the housing 173, and the removable base 175 can serve as a heat sink. Additional lasers can be added into the bottom of the housing 173, into the base 175, and/or, according to the modified implementation shown in FIGS. 26A and 26B, referenced above, a base 186 can be formed (e.g., restructured, as shown, to provide a larger interior) to provide a greater volume for the additional lasers. Also, the base 186 can be formed to have extra ribs or other heat dissipating structures.

In view of the foregoing, it will be understood by those skilled in the art that the methods of the present invention can facilitate formation of laser devices, and in particular diode laser systems. The above-described embodiments have been provided by way of example, and the present invention is not limited to these examples. Multiple variations and modification to the disclosed embodiments will occur, to the extent not mutually exclusive, to those skilled in the art upon consideration of the foregoing description. Such variations and modifications, however, fall well within the scope of the present invention as set forth in the following claims. Additionally, other combinations, omissions, substitutions and modifications will be apparent to the skilled artisan in view of the disclosure herein. As iterated above, any feature or combination of features described and referenced herein are included within the scope of the present invention provided that the features included in any such combination are not mutually inconsistent as will be apparent from the context, this specification, and the knowledge of one of ordinary skill in the art. For example, any of the lasers and laser components including output configurations, and any particulars or features thereof, or other features, including method steps and techniques, may be used with any other structure and process described or referenced herein, in whole or in part, in any combination or permutation. Accordingly, the present invention is not intended to be limited by the disclosed embodiments, but is to be defined by reference to the following additional disclosure in claims format.

What is claimed is:

1. An apparatus, comprising:
an excitation source comprising at least one laser diode within a system; and
a handpiece comprising (a) a disposable, bendable tip cannula, (b) an output fiberoptic operatively coupled to the excitation source and extending at least partially through the bendable tip cannula, the output fiberoptic having a proximal end aligned to receive electromagnetic energy from the excitation source and a distal end adapted to emit the electromagnetic energy away from the handpiece, and (c) a region having a position in a vicinity of the proximal end, an opacity that is less than that of the bendable tip cannula, and a construction that causes an appearance of the region to change when the output fiberoptic emits the electromagnetic radiation from the distal end.

2. The apparatus as set forth in claim 1, wherein the excitation source is a laser module within the system.

3. The apparatus as set forth in claim 1, wherein the excitation source is directly coupled to a trunk optical fiber, and the trunk optical fiber is permanently coupled to the system.

4. The apparatus as set forth in claim 1, wherein the system is a diode laser system, and the excitation source is directly and permanently coupled to a trunk optical fiber.

5. The apparatus as set forth in claim 1, wherein the system is a diode laser system, the excitation source is a laser module within the system that is directly coupled to a trunk optical fiber, and the trunk optical fiber extends continuously and without interruption, interface, or coupling from a permanent connection at the laser module all of the way to the handpiece.

6. The apparatus as set forth in claim 1, wherein (a), (b) and (c) form a disposable output tip that is removably connected at a distal end of the handpiece, and wherein the apparatus further comprises a trunk optical fiber that extends continuously and without interruption, interface, or coupling from a permanent connection at the excitation source all of the way to, and through at least a part of, the handpiece.

7. The apparatus as set forth in claim 1, wherein (a), (b) and (c) form a disposable output tip that is removably connected at a distal end of the handpiece, and wherein the apparatus further comprises a trunk optical fiber that extends continuously and without interruption, interface, or coupling from a permanent connection at the excitation source all of the way to the handpiece and through substantially all of the handpiece, and terminates at the distal end of the handpiece.

8. The apparatus as set forth in claim 1, wherein the apparatus is configured to output laser energy having a wavelength of about 915 microseconds, about 940 microseconds, about 960 microseconds, or about 980 microseconds, and wherein the apparatus is configured to output the laser energy in a continuous wave or quasi-continuous wave mode.

9. The apparatus as set forth in claim 1, wherein the apparatus is configured to output pulsed laser energy with a pulse duration and a pulse interval that are both on the order of microseconds.

10. The apparatus as set forth in claim 1, wherein the apparatus is configured to output pulsed laser energy with a pulse duration of about 50 microseconds or less and a pulse interval of about 450 microseconds or more.

11. The apparatus as set forth in claim 1, wherein:
the apparatus is configured to output pulsed laser energy with an independently adjustable pulse duration that can be adjusted independently of the pulse interval.

12. The apparatus as set forth in claim 1, wherein:
the apparatus is configured to output pulsed laser energy with an independently adjustable pulse interval that can be adjusted independently of the pulse duration.

13. The apparatus as set forth in claim 1, wherein:
the pulse duration may be varied by a user without varying the pulse interval and wherein the pulse interval may be varied by a user without varying the pulse duration.

14. The apparatus as set forth in claim 1, wherein:
the pulse duration may be varied by a user to a greater or lesser degree than a varying the pulse interval and wherein the pulse interval may be varied by a user to a greater or lesser degree than a varying the pulse duration.

15. The apparatus as set forth in claim 1, wherein the proximal end of the output fiberoptic is at least partially surrounded by the region.

16. The apparatus as set forth in claim 1, wherein the bendable tip cannula is constructed not to glow when the output fiberoptic emits the electromagnetic radiation from the distal end.

17. The apparatus as set forth in claim 1, wherein the region is a ferrule.

18. The apparatus as set forth in claim 1, wherein the excitation source is configured to output an aiming beam and the region is a ferrule that glows with a color of the aiming beam.

19. The apparatus as set forth in claim 1, wherein the ferrule has a clear transparency corresponding to a color and transparency of water.

20. The apparatus as set forth in claim 1, wherein the ferrule has a transparency with a slight hue of one or more colors.

* * * * *